United States Patent
Kellnberger et al.

(10) Patent No.: US 12,343,199 B2
(45) Date of Patent: Jul. 1, 2025

(54) MINIATURIZED INTRAVASCULAR FLUORESCENCE-ULTRASOUND IMAGING CATHETER

(71) Applicant: The General Hospital Corporation, Boston, MA (US)

(72) Inventors: Stephan Kellnberger, Norwood, MA (US); Vasilis Ntziachristos, Graefelfing (DE); Dmitry Bozhko, Munich (DE); Farouc Jaffer, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 579 days.

(21) Appl. No.: 15/734,622

(22) PCT Filed: Jun. 4, 2019

(86) PCT No.: PCT/US2019/035431
§ 371 (c)(1),
(2) Date: Dec. 3, 2020

(87) PCT Pub. No.: WO2019/236606
PCT Pub. Date: Dec. 12, 2019

(65) Prior Publication Data
US 2021/0153840 A1    May 27, 2021

Related U.S. Application Data

(60) Provisional application No. 62/681,272, filed on Jun. 6, 2018.

(51) Int. Cl.
*A61B 8/12* (2006.01)
*A61B 8/00* (2006.01)

(52) U.S. Cl.
CPC .............. *A61B 8/12* (2013.01); *A61B 8/4416* (2013.01); *A61B 8/445* (2013.01); *A61B 8/5261* (2013.01)

(58) Field of Classification Search
None
See application file for complete search history.

(56) References Cited

U.S. PATENT DOCUMENTS 10,076,248 B2    9/2018    Rozental
10,234,676 B1*   3/2019    Elmaanaoui ........... G02B 23/26
(Continued)

FOREIGN PATENT DOCUMENTS

CN    103462644 A    12/2013
JP    2009183416 A    8/2009
(Continued)

OTHER PUBLICATIONS

International Searching Authority. International Search Report and Written Opinion for application PCT/US2019/035431. Mailed on Jul. 31, 2019. 15 pages.

*Primary Examiner* — Shahdeep Mohammed
(74) *Attorney, Agent, or Firm* — QUARLES & BRADY LLP

(57) ABSTRACT

A hybrid NIRF/IVUS imaging probe containing i) a spatially-truncated optical lens a substantially-planar surface of which is inclined with respect to an axis to reflect light, transmitted between proximal and distal ends of the probe, internally into a body of the lens, and ii) an acoustic transducer disposed sequentially with the optical lens on the axis of the probe while, at the same time, the optical and electrical members of the probe transmitting the radiative and mechanical energies (which the probe exchanges with a target bodily vessel) are parallel to one another within the housing of the probe. A method for operating the probe resulting in formation of spatially co-registered optical and acoustic images of the target. Related imaging system and computer-program product.

17 Claims, 16 Drawing Sheets

(56) References Cited

U.S. PATENT DOCUMENTS

| | | | |
|---|---|---|---|
| 2014/0323860 A1 | 10/2014 | Courtney | |
| 2015/0005628 A1 | 1/2015 | Itoh | |
| 2015/0272445 A1* | 10/2015 | Rozental | A61B 8/445 |
| | | | 600/407 |
| 2016/0206290 A1* | 7/2016 | Itoh | A61B 8/461 |
| 2016/0270669 A1* | 9/2016 | Tokida | A61B 5/02007 |
| 2017/0181728 A1 | 6/2017 | Tokida | |
| 2020/0046283 A1* | 2/2020 | Tearney | A61B 5/0084 |

FOREIGN PATENT DOCUMENTS

| | | | |
|---|---|---|---|
| JP | 2013121520 A | 6/2013 | |
| JP | 2016174809 A | 10/2016 | |
| WO | 2015003449 A1 | 1/2015 | |
| WO | 2016047772 A1 | 7/2017 | |

\* cited by examiner

TR: Tapered region of the fiber

TR: Tapered region of the fiber

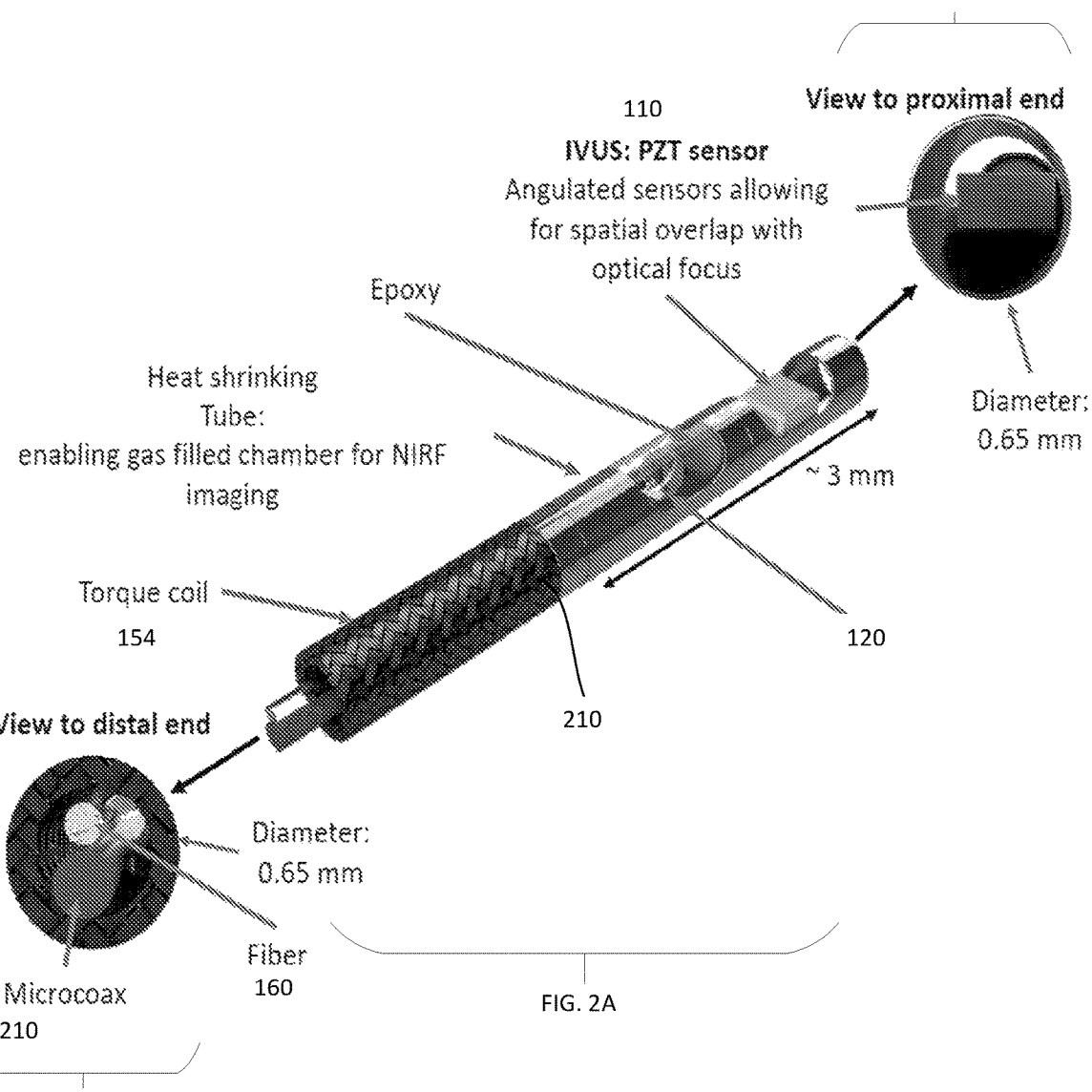

| NIRF-IVUS CATHETER | V1.0 | NEW - V2.0 (TESTED IN VITRO) | NEW - V3.0 (IN PRODUCTION) | IVUS | NIRS -IVUS |
|---|---|---|---|---|---|
| PROXIMAL SHAFT | 1.5 MM \| 4.5F | 1.13MM \| 3.4F | 1.0MM \| 3F | 1.0MM \| 3F | 1.2MM \| 3.6F |
| CATHETER PROFILE | ~1.1MM \| 3.3F | 0.65MM \| 1.95F | 0.55MM \| 1.65F | 0.6MM \| 1.8F | N/A |
| IVUS FREQUENCY (MHZ) | 40MHZ | 40MHZ | 40MHZ | 40MHZ | 40MHZ |
| IVUS RESOLUTION AXIAL (μM) | 150 | 35 | 35 | 38 | N/A |
| OPTICAL BEAM FWHM | >1MM | <450 μM | <450 μM | N/A | N/A |
| DESIGN | PRISM | BALL LENS | BALL LENS | N/A | PRISM |
| ARRANGEMENT | PARALLEL | SERIAL | SERIAL | N/A | OPPOSED |

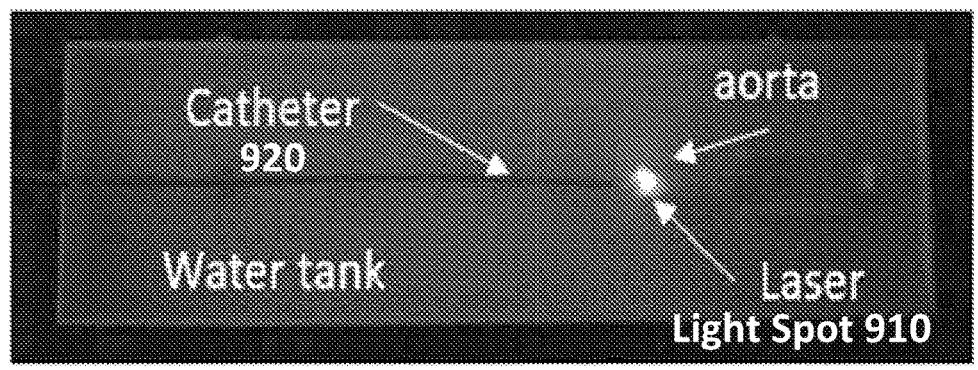
FIG. 9
FIG. 10A
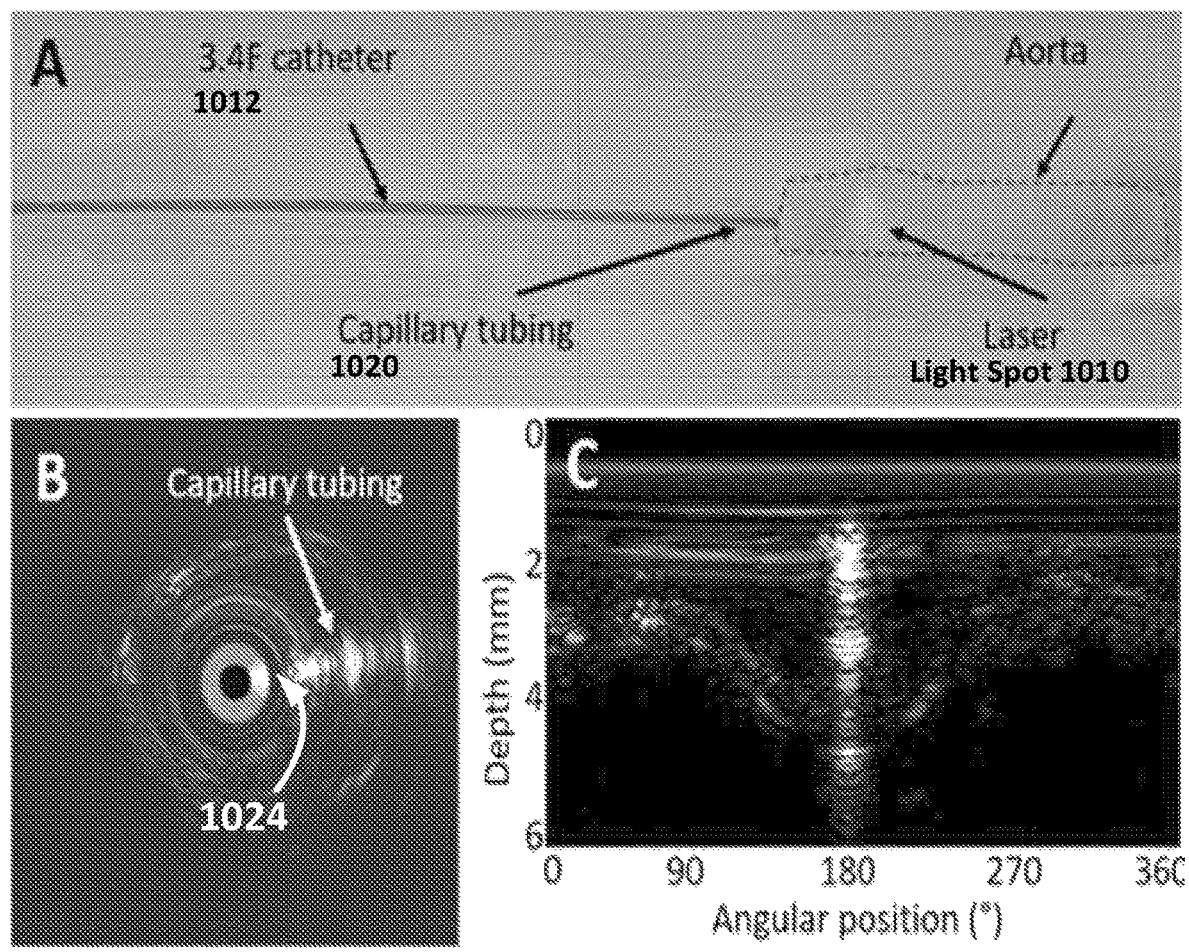
FIG. 10B
FIG. 10C

MINIATURIZED INTRAVASCULAR FLUORESCENCE-ULTRASOUND IMAGING CATHETER

CROSS-REFERENCE TO RELATED APPLICATIONS

This application is a National Stage of the International Application No. PCT/US2019/0035431 filed Jun. 4, 2019 and now published as WO 2019/236606, which claims the benefit of U.S. Provisional Patent Application No. 62/681,272, filed on Jun. 6, 2018. The disclosure of each of the above-identified patent applications is incorporated by reference herein, for all purposes.

STATEMENT REGARDING FEDERALLY SPONSORED RESEARCH

This invention was made with government support under HL122388 awarded by the National Institutes of Health. The government has certain rights in the invention.

TECHNICAL FIELD

Intravascular ultrasound (IVUS) procedure is the current clinical standard in intravascular imaging and is used for assessing anatomical characteristics of cardiovascular disease. Standalone IVUS imaging resolves structural features of cardiovascular disease. To improve imaging beyond collecting only anatomical information, related art combined the structural features related to the IVUS procedure with those facilitating the near-infrared fluorescence (NIRF) molecular imaging. The hybrid NIRF-IVUS-enabled catheter enables simultaneous visualization of both pathophysiological and biological features of cardiovascular disease. Such combinations were empirically tested during the NIRF-IVUS imaging procedure of animals in vivo; however, significant limitations of current NIRF-IVUS catheters of related art are the large size of the NIRF-IVUS catheter that does not satisfy the clinical standards (in particular, with >1.5 mm diameter, as opposed to clinical standard IVUS which are ~1 mm in diameter), and the lack of optical focus from prism-based solutions of related art. These two features limit high-quality, clinically safe NIRF-IVUS imaging of coronary arteries, and the solutions that allow overcoming these limitations have not been reported thus far.

SUMMARY

An embodiment of the present invention provides a method for operating an imaging probe having an axis and a sheath. The method includes at least the steps of: (i) transmitting light inside an optical member that extends along the axis inside the sheath between and connects the proximal end of the probe and an optical transceiver; and (ii) transmitting an electrical signal via an electrically-conducting member extending inside the sheath parallel to the optical member and connecting the proximal end of the probe and an acoustic transducer. Here, the optical transceiver is directly affixed to a distal end of the optical member and the acoustic transducer and the optical transceiver are disposed in sequence with one another along the axis. The method may additionally include the step of reflecting such light from a substantially-planar surface of the optical transceiver (which surface is inclined—that is, is neither parallel nor perpendicular to—with respect to an optical axis of the optical member; the reflection occurs internally in and into a body of the optical transceiver. In substantially any implementation, the method may additionally include at least one of the following: (a) outcoupling the light, that has been reflected internally into the body of the optical transceiver by the substantially-planar surface, through a spatially-curved surface of the optical transceiver into an ambient medium surrounding the optical transceiver to form a first beam of excitation light; and (b) coupling light, that has been collected by the optical transceiver through the spatially-curved surface of the optical transceiver from the ambient medium and reflected internally into the body of the optical transceiver by the substantially-planar surface, into the optical member to form a fluorescence signal delivered to the proximal end.

In any of the above-defined implementations, the specific implementation of the step of transmitting light includes (1) transmitting light through the optical transceiver that is directly attached to the distal end of the optical member at a spatially-curved surface of the optical transceiver; and/or (2) transmitting light through a fluid that is sealed in a chamber containing said optical transceiver and that separates said optical transceiver from the sheath. Alternatively or in addition, the transmission of light through the fluid may include transmission of light through gas.

Alternatively or in addition, the implementation of the method may include generating mechanical energy and directing such mechanical energy between a surface of the acoustic transducer (which surface is inclined with respect to the axis) and the target. In a specific implementation of this latter embodiment, at least one of the following conditions may be satisfied: (a) wherein the mechanical energy includes a second acoustic beam generated by the acoustic transducer; and further comprising spatially overlapping the first beam of the excitation light (outcoupled through the sheath from the optical transceiver upon reflecting the light from a substantially-planar surface of the optical transceiver and transmitting such light through a spatially-curved surface of the optical transceiver) with the second acoustic beam delivered through the sheath, to define an area containing both irradiated with the first beam and insonated with the second beam; and (b) wherein the mechanical energy includes a third acoustic beam formed at the target in response to the target being insonated with the second beam. This method may further include the steps of positioning the so-defined area at the target to cause the target to produce a fluorescent light and an acoustic energy; and collecting the fluorescent light by the optical member upon reflecting the fluorescent light by the substantially-planar surface while transforming the acoustic energy to a return electrical signal to co-register the fluorescent light and the return electrical signal by electronic circuitry operably connected to the probe at the proximal end. In any case, the step of spatially-overlapping includes spatially-overlapping the first and second beams at a location on a plane containing the axis of the probe.

Alternatively or in addition, the step of transmitting light may include transmitting a first light and a second light through the optical transceiver under conditions that the optical transceiver has a body limited by a first spatially-curved surface and a second substantially-planar surface, and when the second light is emitted at a location outside of the sheath that has been irradiated with the first light. Alternatively or in addition, each of the steps of transmitting the light inside the optical member and transmitting the electrical signal via the electrically-conducting member may include transmitting energy inside the sheath having a diameter smaller than 1.2 millimeters. Alternatively or in addition, each of the steps of transmitting the light inside the optical member and transmitting the electrical signal via the electrically-conducting member may include transmitting energy inside the sheath having a diameter smaller than 0.7 millimeters. (In any of these cases, the imaging probe is structured to includes a torque coil disposed inside the sheath and configured to rotate during the operation, transmitting the energy includes transmitting the energy inside the torque coil.) Alternatively or in addition, in a given implementation of the method at least one of the following conditions may be satisfied:

(i) transmitting the light inside the optical member includes transmitting light through a lensed optical fiber;

(ii) transmitting the light inside the optical member includes transmitting light through an optical fiber terminated with a cleaved reflective surface;

(iii) the operation of the imaging probe is devoid of using an optical prism; and (iv) the acoustic transducer and the optical transceiver are sequentially disposed on the axis of the probe.

In substantially any implementation, the method may additionally include the steps of a) receiving a return electrical signal acquired with the acoustic transceiver from a first location outside of the sheath to form a first image representing an anatomical structure at the first location; and b) receiving a return optical signal acquired in transmission through the optical transceiver from a second location outside of the sheath to form a second image of a molecular structure characterizing the second location, wherein the return optical signal contains fluorescence generated at the target in response to the target being irradiated with excitation light delivered from the proximal end of the optical member and reflected by the substantially-planar reflector internally into the body of the optical transceiver. These steps are implemented with the use of optoelectronic circuitry at the proximal end of the probe.

Embodiments of the invention additionally provide an imaging probe having a probe axis and containing: an optically-transparent member extending from a proximal end of the probe to a distal end of the probe in parallel to the probe axis and terminated with an optical transceiver integrally affixed to the optically-transparent member at the distal end of the probe; and an electrically-conducting member extending from the proximal end of the probe to the distal end of the probe in parallel to the optically-transparent member and terminated with an acoustic transducer. Here, the acoustic transducer and the optical transceiver are disposed sequentially on the probe axis. The embodiment may additionally include a housing element at least partially-enclosing the optically-transparent member, the optical transceiver, the electrically-conducting member, and the acoustic transducer and dimensioned to not exceed 1.2 mm in diameter. Alternatively or in addition. The housing element is configured to not exceed 0.7 mm in diameter. (In any of these cases, the imaging probe additionally includes a torque coil disposed inside the sheath and configured to rotate during the operation, and each of the optically-transparent member and the electrically-conducting member is disposed inside the torque coil.)

In substantially any embodiment in which the housing element is present, the housing element includes first and second apertures in a wall of the housing element, the first aperture being optically-transparent and the second aperture being acoustically-transparent, the first and second apertures spatially-coordinated with the optical transceiver and the acoustic transducer, respectively. (In a specific case, these first and second apertures are formed on the same side of the housing with respect to the axis of the probe.) In substantially any embodiment, the optical transceiver is configured as a plano-convex optical lens with the planar surface of the optical lens is slanted (inclined, neither perpendicular nor parallel to) with respect to an axis of the optically-transparent member.

The acoustic transducer and the optical transceiver may be oriented such that a first beam of light (that has been delivered via the optically-transparent member, reflected from a substantially-planar surface of the optical transceiver, and transmitted through the optical transceiver to a medium surrounding the probe) and a second beam of acoustic energy (generated by the acoustic transducer in response to the electrical signal that has been delivered via the electrically-conducting member from the proximal end to the medium) overlap at a location of the medium surrounding the probe. In a specific case, such location is defined in a plane containing an axis of the housing.

Substantially in any embodiment, the imaging probe may be configured to include a fluidly-sealed chamber containing at least the optical transceiver and filled with a fluid separating the optical transceiver from a wall of such chamber. Substantially in any embodiment, the optical transceiver may be formatted to have a body spatially-limited by a spatially-curved surface and a substantially-planar surface and directly affixed to the optically-transparent member at the spatially-curved surface. Substantially in any embodiment, the imaging probe is devoid of (does not include) an optical prism.

BRIEF DESCRIPTION OF THE DRAWINGS

The invention will be more fully understood by referring to the following Detailed Description of Specific Embodiments in conjunction with the Drawings, of which:

FIG. 1A: The IVUS sensor is located at the distal end of the embodiment of the catheter after the NIRF sensor. FIG. 1B: The NIRF sensor is located at the distal end of the embodiment of the catheter after the IVUS sensor.

FIG. 1E: side view; FIG. 1F: top view (along the arrow AA).

FIG. 1G: side view; FIG. 1H: top view (along the arrow BB).

FIGS. 2A, 2B, 2C: An embodiment of the hybrid catheter of the invention shown without a catheter sheath in: FIG. 2A—perspective view; FIG. 2B—view along the axis towards the distal end; and FIG. 2C—view along the axis towards the proximal end.

FIG. 5A: Longitudinal view of the catheter. Different steering angles allow for spatial overlap of optical and ultrasound beams to enable spatial co-registration of IVUS and NIRF images. FIG. 5B: Longitudinal view of the catheter. Implementation where the IVUS sensor and NIRF sensor windows are facing in different directions. FIG. 5C: Axial view of the catheter. Implementation of the catheter where the optical beam and IVUS beam are dislocated at an angle γ on the axial direction.

FIG. 6A illustrates a model of the catheter equipped with key features configured for clinical application (such as monorail access and flushing capability), while FIG. 6B shows the embodiment of the catheter inserted in a 3.4 F catheter sheath.

FIG. 9 is a depiction of an optical signal acquired during the pull-back of an embodiment of the catheter of the invention in a rabbit aorta ex vivo.

FIGS. 10A, 10B, 10C provide illustration of the ex vivo experiment and the NIRF-IVUS image reconstruction. FIG. 10A shows a 3.4 F embodiment of the catheter of the invention a resected aorta vessel. Capillary tube with AF750 dye is positioned next to the catheter in the vessel to enable NIRF contrast. FIG. 10B presents an overlap of the NIRF image and the IVUS image showing the aorta and the capillary tube in both images. FIG. 10C: a depth-profilometric (spatially unwrapped) IVUS image of the aorta vessel.

Figure 1A:
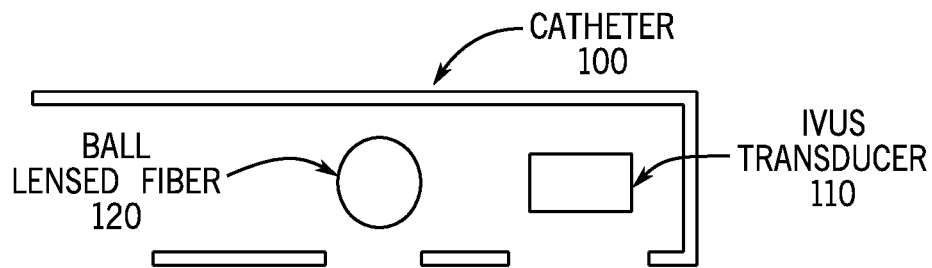
FIGS. 1A, 1B are schematic showings of examples of spatial disposition of the NIRF and IVUS sensors in the embodiment of the catheter.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Features of the specific implementation(s) of the idea of the invention is described with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

The invention as recited in claims appended to this disclosure is intended to be assessed in light of the disclosure as a whole.

A persisting problem of inability of related art to provide a sub-3 F catheter or probe, configured for simultaneous molecular and structural imaging, is solved by organizing the sensors of the hybrid NIRF-IVUS probe in a serial fashion along the axis of the embodiment of the catheter while, at the same time, disposing the optical- and acoustic-signal-transmitting elongated members (that operably connect the corresponding sensors with appropriate electronic and/or optical circuitry cooperated with the proximal end of the catheter) substantially parallel to one another and the axis of the catheter. In particular, the proposed solution provides the hybrid NIRF-IVUS catheter having an outer dimeter of 0.55 mm or smaller, suitable for clinical imaging and dimensioned to be no larger than a standalone clinical IVUS catheter of related art.

A problem of inability of related art to maintain the spatial characteristics of the optical beam, used in operation of the optical channel of the embodiment, substantially constant in the vicinity of the termination of the optical channel at the distal end of the imaging probe is solved by avoiding the use of optical prismatic elements as part of the optical channel (in particular, avoiding the use of a prism that is attached to the cleaved optical fiber by means of an adhesive and that provides for about 90% or higher reflection of the incoming optical beam, transmitting such beam between the optical channel of the probe and the ambient medium). Instead, embodiments of the invention are structured to terminate the optical channel with a judiciously-shaped lens having a curved surface and a substantially-planar surface that is inclined with respect to the axis of the optical channel, while at the same time isolating the optical-fiber-terminating lens within a chamber at least partially-filled with fluid (in one implementation—an appropriate gaseous substance, in a related optional implementation—partially filled with liquid).

A persisting operation shortcoming of embodiments of related art, that manifests in structural difficulties of co-registration of the NIRF/IVUS images is solved by configuring each of the ultrasound transducer and a planar reflecting surface of the to be inclined with respect to the axis of the catheter at predefined angles and/or judiciously configuring the spatial orientation of the ultrasound-transparent and optically-transparent windows of the ferrule that contains the optical and acoustic sensors.

Specifically, in accordance with preferred embodiments of the present invention, methods and apparatus are disclosed for embodiments of a miniaturized version of a structurally-integrated NIRF-IVUS catheter that incorporates an optical fiber equipped with a judiciously-dimensioned lens (in one example—in the shape of an appropriately truncated sphere/ball lens) rather than with the current optical prism-complemented models of related art. So structured, the embodiments are appropriately miniaturized to satisfy critical dimensional standards of IVUS procedures and improve, in operation, collection of fluorescence light in parallel with ultrasound signal detection from the intended target. Notably, in contradistinction with related art, the hybrid NIRF-IVUS design is about the same size as that of clinically-employed IVUS catheters and comes with improved NIRF signal sensitivity compared to previous designs, based on a novel implementation of a lensed fiber that preserves its refractive index in a specialized gas chamber, thereby allowing for highly focused imaging and a miniaturized solution. The specifically-lensed optical fiber, utilized in embodiments of the invention, additionally facilitates:

increased NIRF sensitivity due to higher light fluence on target a straightforward implementation enabling mass production of the catheter' a very small catheter size (about 0.55 mm) allowing for clinically viable NIRF-IVUS imaging of coronary arteries; as well as an ability to steer the optical beam through appropriate selection of the polishing/reflection angle of the lensed fiber, thereby enabling the spatial overlap of ultrasound and optical beams for NIRF-IVUS image co-registration.

Embodiments of the NIRF-IVUS catheter of the invention is configured to be used in intravascular imaging of cardiovascular disease in preclinical and clinical environments. The new catheter may also be useful for pharmacotherapeutic trials to test new drugs (such as PCSK9 inhibitors or cankinumab, for example). Our catheter with the NIRF-IVUS technology could also be useful for testing new investigational drugs and stents, as it can be coupled with different molecular probes for inflammation, fibrin, endothelial leak, etc.

Figure 1B:
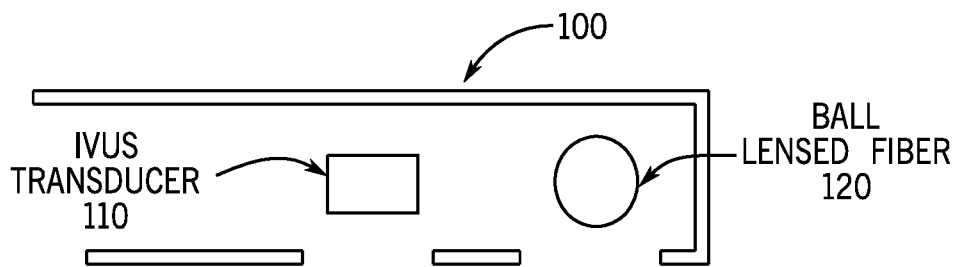

According to the idea of the invention, an embodiment of the hybrid NIRF-IVUS catheter includes an ultrasound transducer and an optical lens configured as a truncated ball lens—both in the distal portion of the embodiment—to guide light and sound to the chosen target (a vessel wall, in case of intravascular applications). A person of ordinary skill in the art is well aware of the fact that use of a lensed fiber for a NIRF-IVUS system—let alone an optical fiber complemented with an embodiment of the truncated ball lens—is not currently realized with other IVUS and/or NIRF devices, that conventionally use an optical prism to couple/outcouple optical signals to and from the optical fiber of the catheter. To this end, FIGS. 1A, 1B schematically illustrate mutual spatial disposition of the IVUS transducer component 110 and the lens 120 of the fiber-optic component (in these figures representing the distal end of the fiber-optic component) of the embodiment 100 of the catheter of the invention in the distal portion 130 of the embodiment. The IVUS transducer 110 and the NIRF lensed fiber with the lens 120 are shown positioned in a serial orientation to facilitate a slim design of the miniaturized catheter. For example, as shown in FIG. 1A, the IVUS transducer 110 may be located closer to the distal end of the catheter while the NIRF lensed fiber is positioned before the IVUS transducer 110. As another example (FIG. 1B), the end of the NIRF sensor (defined by the lens 120) may be positioned closer to the distal end of the catheter than the end of the IVUS sensor (defined by the transducer 110).

Focusing of optical radiation with the appropriately-shaped lens can be additionally improved and/or modified with the use of a combination of lensed fibers, microlenses, and/or gradient index optics, as desired, at least one of which can be positioned between the fiber and the lens or after the lensed fiber. For example, a GRIN lens (gradient-index lens, also called graded-index lens) located before and/or after the lensed fiber can be used to improve focusing of the lensed fiber.

The combination of ultrasound transducer/sensor and a lensed optical fiber is appropriately structured to make that the embodiment is operably compatible with a fluid-filled environment. Specifically, as discussed below, to assist a lensed fiber to function in the normal, typical IVUS environment (which is water/saline immersed), the lens of the fiber-optical component of the embodiment was isolated into a gaseous environment (e.g., air)-filled closed chamber to ensure the preservation/fixation of the operational value of the refractive index of the lens and, accordingly, its numerical aperture. Example features of the new NIRF-IVUS catheter using a lensed fiber for NIRF signal detection include the use of smaller fibers as compared to those utilized in prism-based solutions of related art. (Indeed, the prism-containing optical channels of the imaging probes of related art typically utilize optical fibers with dimensions of about 200 micron diameter core/220 micron diameter cladding or larger.)

Figure 1C:
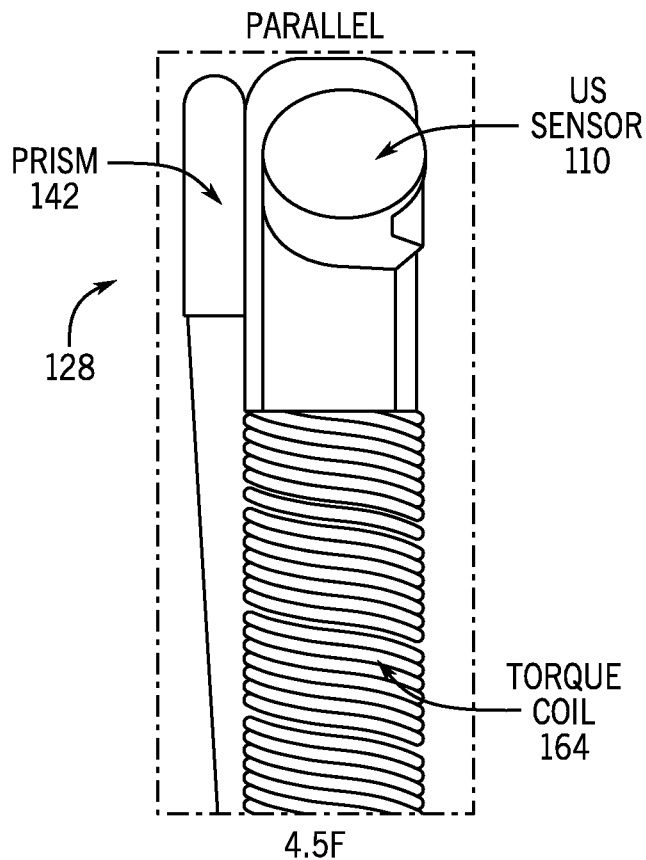
FIGS. 1C and 1D provide comparison of the parallel spatial arrangement of the NIRF-IVUS embodiment of related art with a serial (sequential) arrangement of the embodiment of the invention.
Figure 1D:
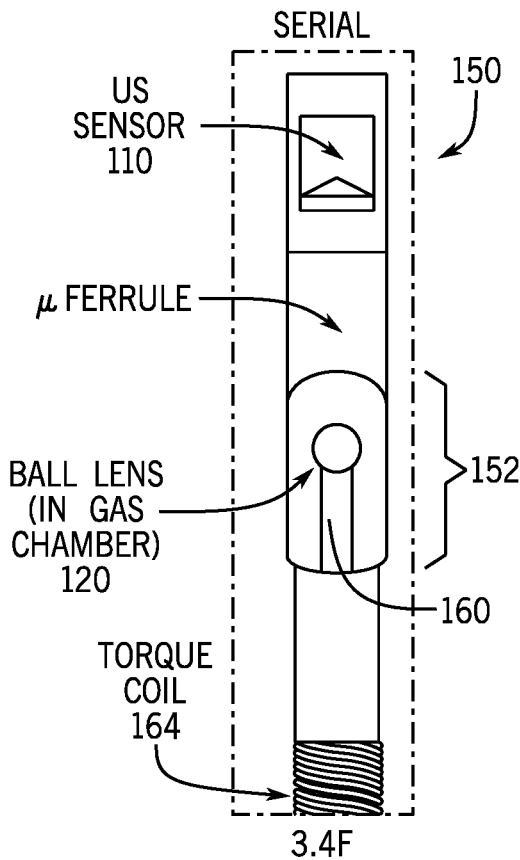

Serial/Sequential Axial Spatial Arrangement of the Radiative and Acoustic Transceivers. FIG. 1C provide an illustration of the embodiment of the related art, specifically— the embodiment 140 (the optical channel of which is structured around the optical prism 142 and in which the ultrasound and optical channels are arranged in parallel to one another), described, for example, in U.S. Pat. No. 10,076,248, the disclosure of which is incorporated by reference herein. In contradistinction with related art, FIG. 1D presents the embodiment 150 of the present invention, with serially-disposed US transducer 110 and the lens 120 (juxtaposed to the end of the fiber 160 and located in the chamber 152 (that is filled with fluid, preferably gas) both of which at the same time are disposed on the axis of the probe. One advantageous structuring of the embodiment 150 of the invention over that of related art becomes immediately apparent to a skilled person: the reduction of the overall diameter from 4.5 F to 3.4 F. Notably, in both embodiments the torque coil 154 may be implemented in order to increase mechanical stability and strength of the catheter and/or to protect the signal/fibers/wires that transmit signal to the system from the sensors, to provide flexibility such that the catheter can be maneuvered in the vessel, and to enable maximum transmission of torque to the catheter distal end from the rotating motor-drive unit (MDU) discussed below.

Figure 1E:
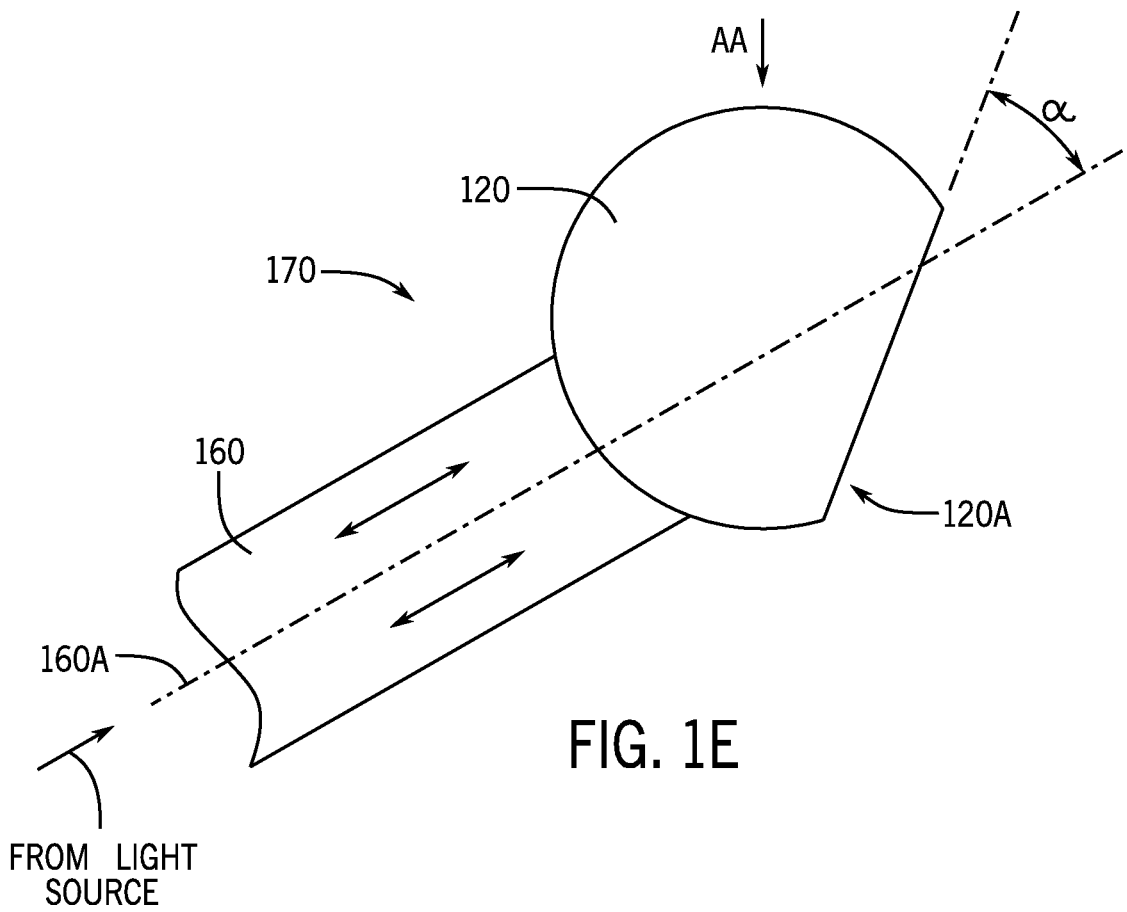
FIGS. 1E, 1F schematically illustrate the optically-transparent member (channel) of the embodiment of the probe terminated with a truncated ball lens that is structured to have a reflecting planar surface of the lens.
Figure 1F:
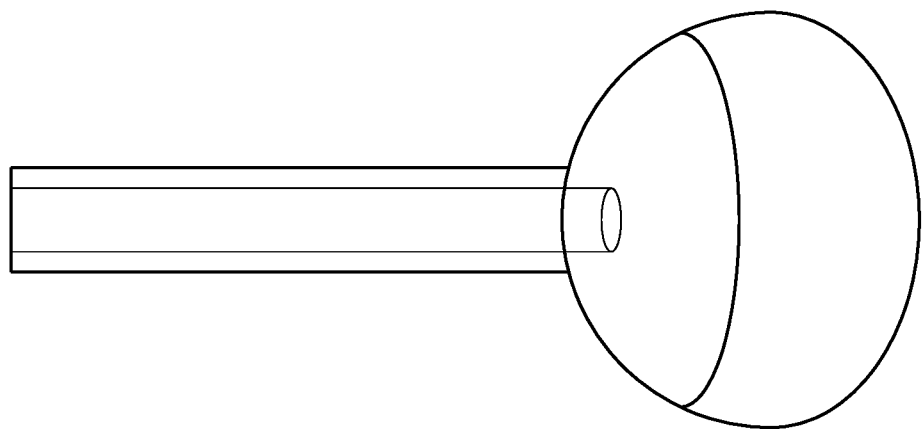

Lensed Optical Channel. In reference to FIGS. 1E and 1F, and depending on the specifics of the particular implementation, bare polishing of a ball lens 120 at specific angle α (defined, for example, with respect to the axis 160A of the optical fiber 160) to form the surface (typically, planar surface) 120A is utilized to provide a reflection efficiency in excess of 80% or even 90% at the reflective surface 120A of the lensed fiber 170. Understandably, the optical reflectance characteristic of the lensed fiber 170, and correspondingly optical transmittance of light from the light source (such as the laser light source to the target) can be altered by appropriately coating optical reflector surface 120A instead of just bare polishing it. In this case, the reflective surface of the lensed fiber will be coated with a highly reflective film after polishing. Depending on the particular implementation, the optical fiber 160 may be either a multimode fiber (MMF), a singlemode fiber (SMF), or a double clad fiber (DCF), that is configured to deliver excitation optical radiation at the first, excitation wavelength along the optical axis 160A from the light source cooperated with proximal end of the optical channel to the truncated lens 120. In the case of a DCF, the excitation wavelength is propagating in the core of the DCF, while fluorescence emission is detected in the cladding of the DCF. The excitation radiation traverses the body of the lens 120 towards the substantially-planar reflector 120A, is reflected by the reflector 120 internally to the lens 120 towards and through the spatially-curved surface of the lens 120 to than a spatially-converging optical beam directed towards the target outside of the lens 120. Empirical data showed that, in operation, more than 90% of the excitation radiation was delivered to the target. The same optical fiber 160 is dimensioned to channel fluorescence (at a wavelengths exceeding 750 nm) that is generated by the target in response to being irradiated with the excitation radiation and then collected through the curved surface of the lens 120A and reflected by the surface 120A and coupled, internally to the lens 120, into the body of the fiber 160.

Figure 1G:
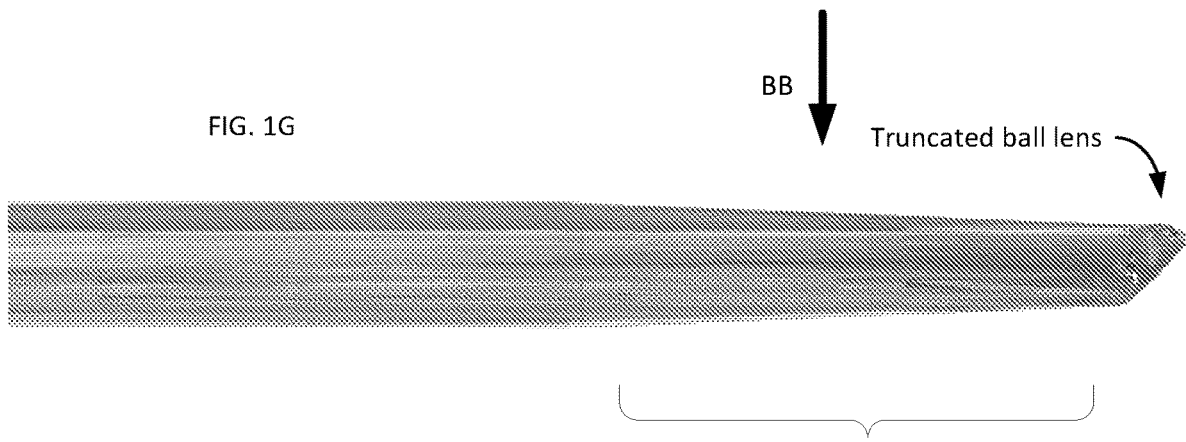
FIGS. 1G, 1H schematically illustrate the optical-transparent member of an embodiment of the invention configured as a spatially-tapered optical fiber terminated with a truncated ball lens defining a reflecting planar surface.
Figure 1H:
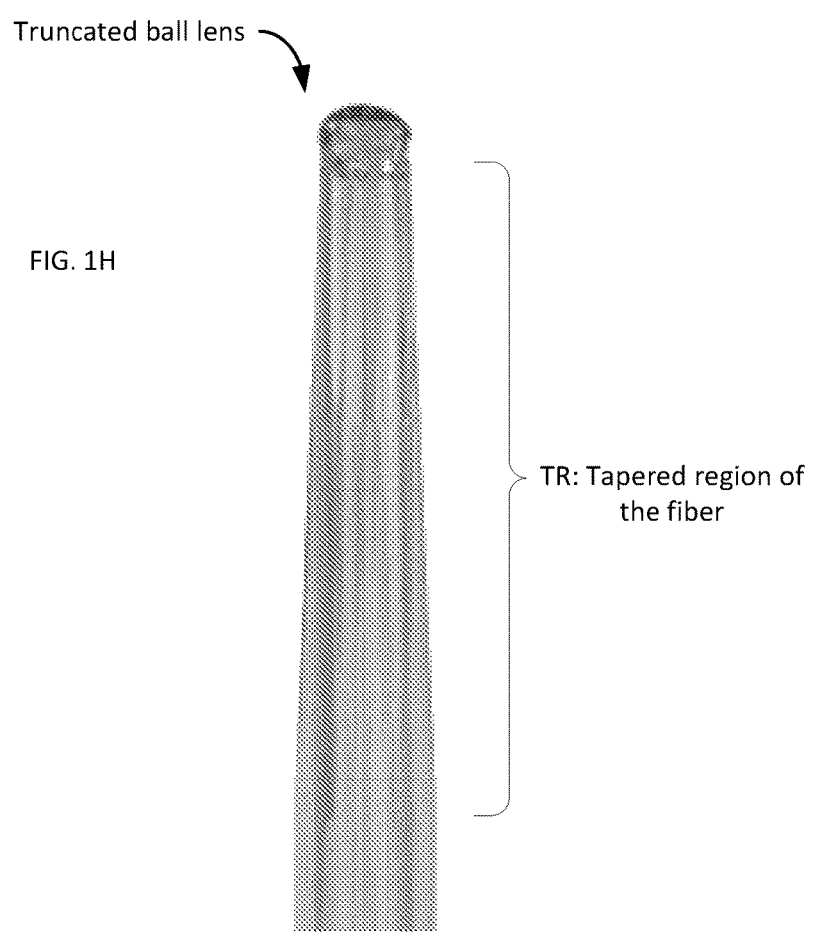

Generally, a particular shape of the lens at the distal end of the fiber optic is not limited to a sphere or ball, but can be chosen to be an elliptical shape, a conical shape (to result in an Axicon lens), a spatially-tapered shape (as schematically illustrated in FIGS. 1G, 1H as an option of the configuration of the optical channel of the probe), and/or any other appropriate shape(s) which can guide and/or focus light as desired. For example, in one implementation the outer surface of the lens can be made to conform to an elliptical surface to correct for astigmatic focus due to the curved shape of the catheter sheath. In a related implementation, the optically-transparent member of the probe (that is, the fiber-optic channel of the probe) maybe configured as an optical fiber terminated with a cleaved and/or polished facet defined at an angle with respect to the axis of the optical fiber (whether additionally coated or not) and without an optical lens element at the end of the fiber.

In one example, the IVUS transducer 110 is implemented based on a single-crystal sensor (such as, but not limited to, PMN-PT, PIN-PMN-PT, LN, or LiNbO3 crystal) and/or conventional PZT ceramics (such as, but not limited to, Pb(Zr, Ti)O3 ceramics) and/or lead-based ultrasound sensor (such as, but not limited to, PbTiO3) and/or a piezoelectric transducer (based, for example, on polyvinylidene fluoride, PVDF, film). Alternatively or in addition, a capacitive micromachined ultrasonic transducer (CMUT) can be used for ultrasound pulse/echo measurements. Alternatively or in addition, the detection of ultrasound detection can also be based on optical interferometric detectors (as known in related art), which may help facilitate high ultrasound frequencies (up to 100 MHz or even 200 MHz) combined with high detection bandwidths.

Gas/Liquid/Solid-filled NIRF Imaging Chamber.

In a regular IVUS imaging environment, the lumen of the catheter sheath is filled with fluids such as saline/water. To this end, and in further reference to FIGS. 1D and 1E, in order to ensure that the optical properties of the optical channel of the embodiment of the invention remain substantially constant and do not change from the measurement of the measurement, the embodiment of the catheter is equipped with at least partially-filled with an appropriately chosen fluid (e.g. air or another gas or other fluid(s)) chamber 152, that optically and spatially separates the lens 120 and/or at least a portion of the lensed fiber 170 from the liquid-filled sheath lumen of the catheter. Such operable isolation of the lens 120 of the fiber 170 from the lumen environment is, in one implementation, facilitated using tubings with high optical transmission and low optical scattering coefficients (e.g. optically transparent medical tubings, optically transparent heat shrinking tubings such as, for example, tubing model number 103-0025 from Nordson Biomedical).

The chamber 152 used for NIRF imaging can be at least partially filled with one or more materials such as gases, fluids, and/or solids exhibiting different refractive indices to control the focusing abilities of the lensed fiber. While most gases have a refractive index of around 1, the chamber can also be at least partially filled with liquids, other fluids, and/or solid materials that alter the refractive index of the optical medium and correspondingly change the focusing properties of the lensed fiber.

In a specific embodiment, the IVUS/NIRF sensors may be placed in a ferrule that can at least partially encapsulate and help protect the sensors from mechanical impacts, as shown in the example of FIGS. 2A, 2B, 2C that illustrate the practical implementation of the catheter without the catheter sheath, where the axial extent of the "head" portion of the catheter (containing the lens in the fluid-filled chamber and the ultrasound transducer inside such ferrule 210) does not exceed 3 mm with the diameter of 0.65 mm, in this specific case. The ferrule can be at least partially made from customized hypotubes (e.g. stainless steel, aluminum, PVC, and/or other materials) containing imaging and sensing windows (holes) to facilitate substantially lossless transmission of optical radiation and ultrasound energy to the target. As an example, the ferrule can contain imaging and sensing windows (readily seen in FIG. 2A) made using precision laser cutting or appropriately-chosen material-etching methods. The IVUS and NIRF sensors may be fixed within the ferrule using epoxy resins, urethane-based adhesives, silicone-based adhesives, and/or other adhesives/glues. The adhesive may fasten the sensors in the ferrule and simultaneously at least partially isolate the NIRF sensor from the fluid environment of the lumen sheath, as shown in FIGS. 2A, 2B, 2C. Electrically-conducting member 220 (such as wire or cable) is used to connect the transducer 110 with the appropriate electronic circuitry (not shown; located at the proximal end of the embodiment).

Figure 3:
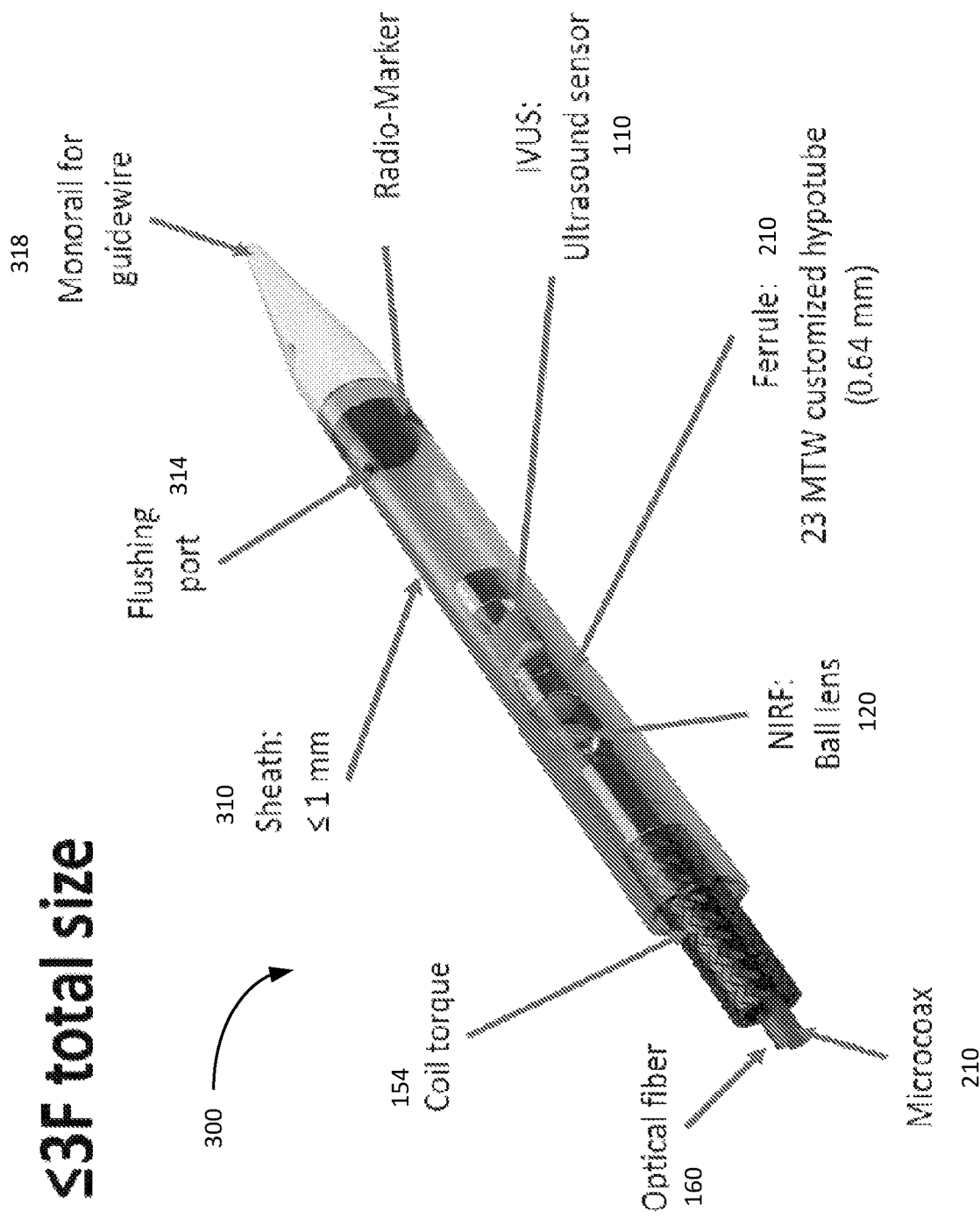
FIG. 3 is a diagram of the embodiment of FIGS. 2A, 2B, 2C with a catheter sheath FIG. 4 provides an outside view of the catheter sheath and catheter telescope only, without the details of the embodiment of the imaging catheter.

Additional details of the embodiment of FIGS. 2A, 2B, 2C are illustrated in FIG. 3, where such embodiment 300 is shown with the catheter sheath 310 the outer diameter of which does not exceed 1 mm. The acoustic (ultrasound) transducer (sensor) 110 is judiciously oriented to have its surface outcoupling, in operation of the transducer, the acoustic beam to the medium surrounding the probe to be inclined with respect to the axis of the probe and disposed on the axis of the probe sequentially with the on-the-probe located truncated optical lens 120. Such angular inclination of the acoustic transducer 110 (labelled in FIG. 2A as "angulated sensor") is devised to ensure the spatial overlap between a focal spot of the optical beam delivered through the optical transceiver 120 to the surrounding medium with the acoustic beam delivered by the acoustic transducer. (Indeed, a person of skill will readily appreciate that embodiments of the related art, employing the optical transducers equipped with optical prisms, do not allow for such spatial overlap, as a result of which spatial co-registration of the mechanical energy received from the target and optical energy, received from the target in form of fluorescent light as a result of excitation of the target with excitation light from the probe, does not occur.) In one implementation, the optical transceiver 120 and the acoustic transducer are judiciously oriented to ensure that such overlap occurs at the location on a plane that contains that axis of the probe.

The embodiment is equipped with the flushing port 314, required for operation of the IVUS modality of the probe in fluid, and the monorail 318 for a guidewire providing support and guidance of the probe mounted upon it. As known in the art, radiomarkers are used to provide an additional degree of freedom of independent determination of the position of the probe in the vessel (which may be of practical use during the angiographic procedure, for example).

Figure 4:
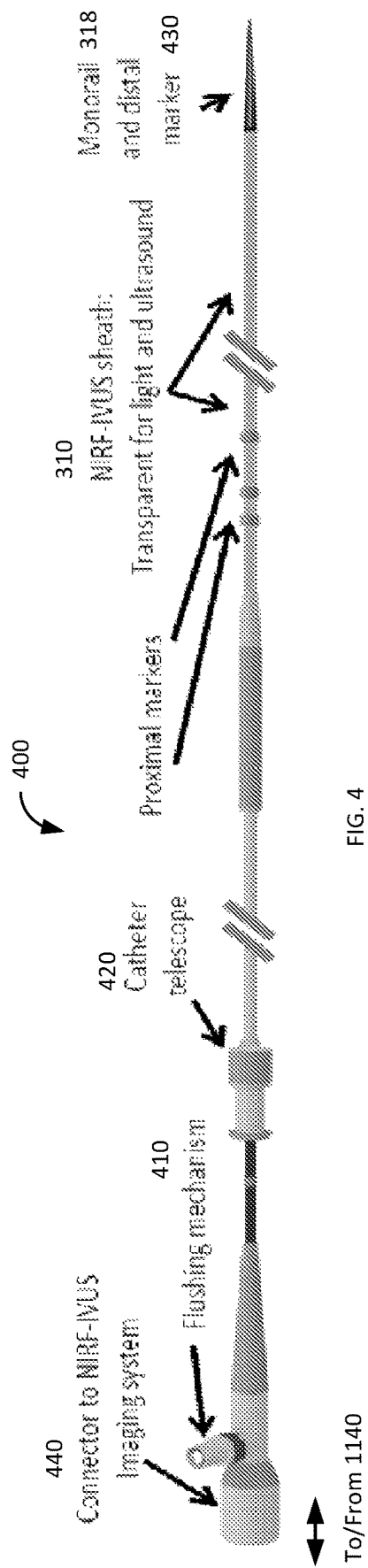

FIG. 4 schematically illustrates a sheath-component 400 of the embodiment of the catheter (without the imaging catheter itself). The flushing mechanism 410 is devised to operate in conjunction with the flushing port 314. The catheter optical telescope 420 is mounted on the judiciously designed static mechanical support and, therefore, remains stationary in the process of the pull-back and rotation procedure during which the optical transceiver may irradiate and, accordingly, collect the return fluorescence signal from the portions of the bodily vessel that are located along a helical curve. The distal radiomarker 430 is, generally, optional. Opto-mechanical connector 440 at the proximal end of the probe is structured as part of the motor-drive unit of the peripheral portion of the overall imaging system, and includes fiber-optic rotary junction or joint and/or slip-ring arrangement configured to uninterruptingly transmit optical and electrical signals between the catheter/probe and the opto-electronic sub-systems of the imaging system of the invention that are discussed below.

(Re)Direction of Beams) of Energy in Space.

According to the idea of the invention, and in further reference to FIG. 2A, the emission angle of the ultrasound beam delivered by the transducer 110 beam is at least partially controlled and/or varied by positioning the transducer 110 at a specific angle with respect to the axis of the probe in the housing/ferrule of the embodiment of the catheter.

Figure 5A:
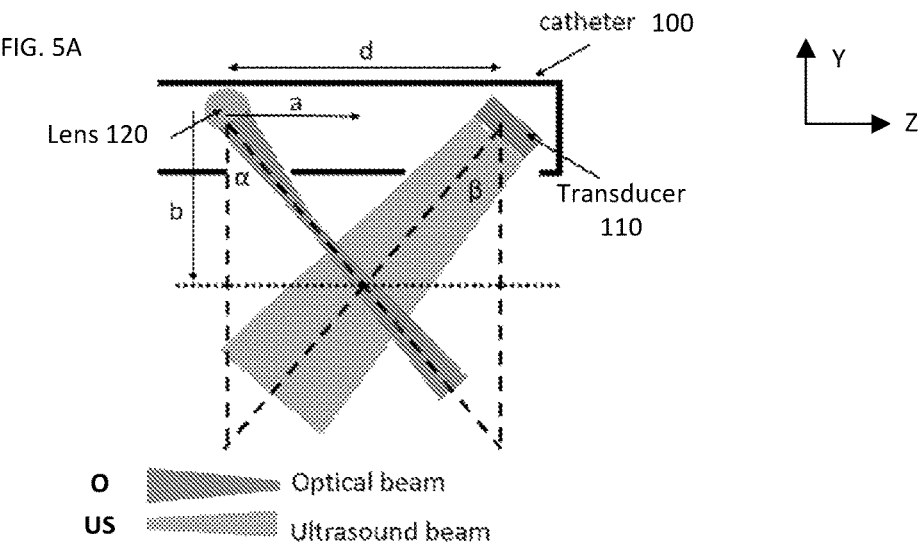
FIGS. 5A, 5B, 5C schematically illustrate certain components of an embodiment of the catheter structured according to the idea of the invention in different views, to show different steering angles of ultrasound and optical beams.
Figure 17:
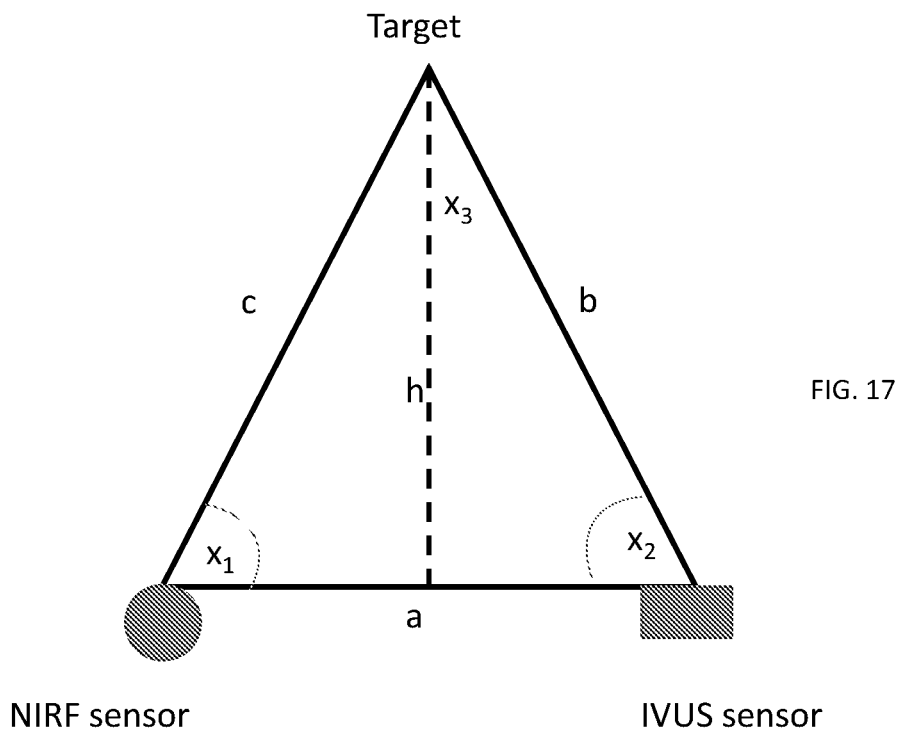
FIG. 17 provides a schematic illustration to spatial positioning of the components of the invention.

Similarly, the lensed fiber 170 allows for steering and/or redirection of the optical beam at different angles, as seen in the azimuthal plane that is transverse to the axis 160A of the fiber) by means of different polishing angles of the lens and/or appropriate orientation of the polished reflector 120A in reference to the azimuthal system of coordinates in such azimuthal plane. Provided such degree of variation is enabled for both the ultrasound and optical beams emanating from the catheter (the lens 120 and the transducer 110, according) through the respectively-corresponding windows in the ferrule 210 (in which case the similar variation of spatial propagation is enabled for the ultrasound and optical signals returned by the target to the corresponding sensors), the ultrasound beam and the optical beam can be appropriately steered and/or directed to spatially overlap and/or intersect with one another, thereby facilitating a simple implementation of spatial co-registration of the reconstructed NIRF and IVUS image. This situation is schematically illustrated in FIG. 5A, and in further reference to the simplified schematics of FIGS. 1A, 1B, 1C. As an example, and in reference to the schematic of FIG. 17, the IVUS transducer 110 and the NIRF sensor (e.g. lensed fiber 170) can be placed at a distance of a=0.25 mm apart and positioned at an angle of $x_1=x_2=83°$ to enable maximum spatial overlap at a distance of h=1 mm from the sensors. In another example, in order to increase the separation between the location of the spatial overlap of the ultrasound beam with the optical beam to h=1 mm, the parameters are as follows: a=0.5 mm, $x_1=x_2=76°$.

As a person of skill will readily appreciate, in practice, in order to acquire 3D images (a helical data matrix), the catheter (in particular, the electrically-conducting member and IVUS sensor 110 and the optical fiber 160 with the truncated lens 120) is rotated about the axis of the catheter to acquire "panoramic/circular data set" (along the circular path, defined by the combination of rotation of the catheter) of the vessel wall, while the combination of such rotation with a pullback of the catheter facilitates the acquisition of a 3D "helical data set" for volumetric image reconstruction.

Figure 5B:
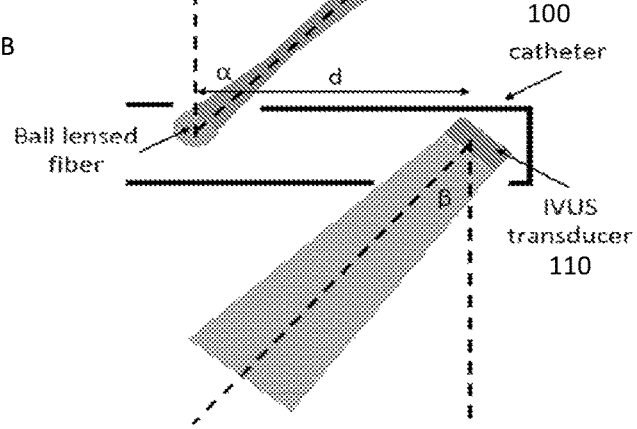
Figure 5C:
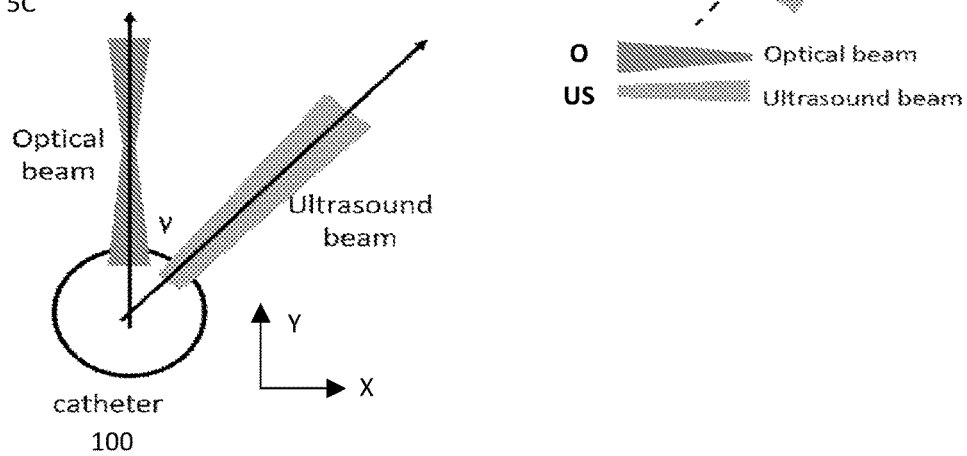

While in a specific embodiment of the invention shown in FIG. 5A the imaging and sensing windows are configured in the ferrule 210 (with respect to the axis of the catheter), as result of which the optical and ultrasound beams are directed to deliver the corresponding optical and acoustic signals to/from the same direction, in a related embodiment illustrated in FIG. 5B such orientation may be appropriately changed. For example, FIG. 5B illustrates the situation when the windows are disposed on the opposite sides of the ferrule with respect to the axis of the catheter, resulting in the appropriately changed spatial orientation of delivery/collection of the optical/acoustic signals. FIG. 5C illustrates the angular separation between the axes of the optical and ultrasound beams (in the azimuthal plane) of less than 90 degrees.

Figure 6A:
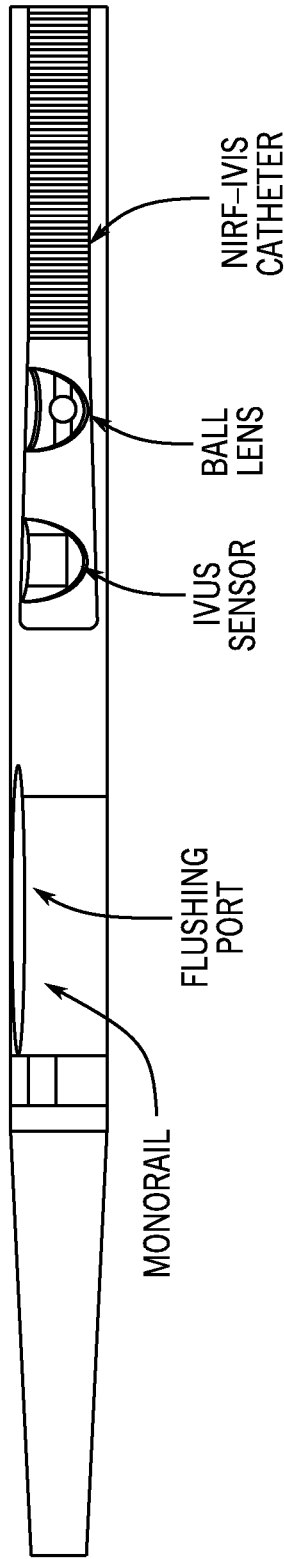
FIGS. 6A, 6B: A schematic of a fully-assembled embodiment of the catheter of the invention. Here.
Figure 6B:
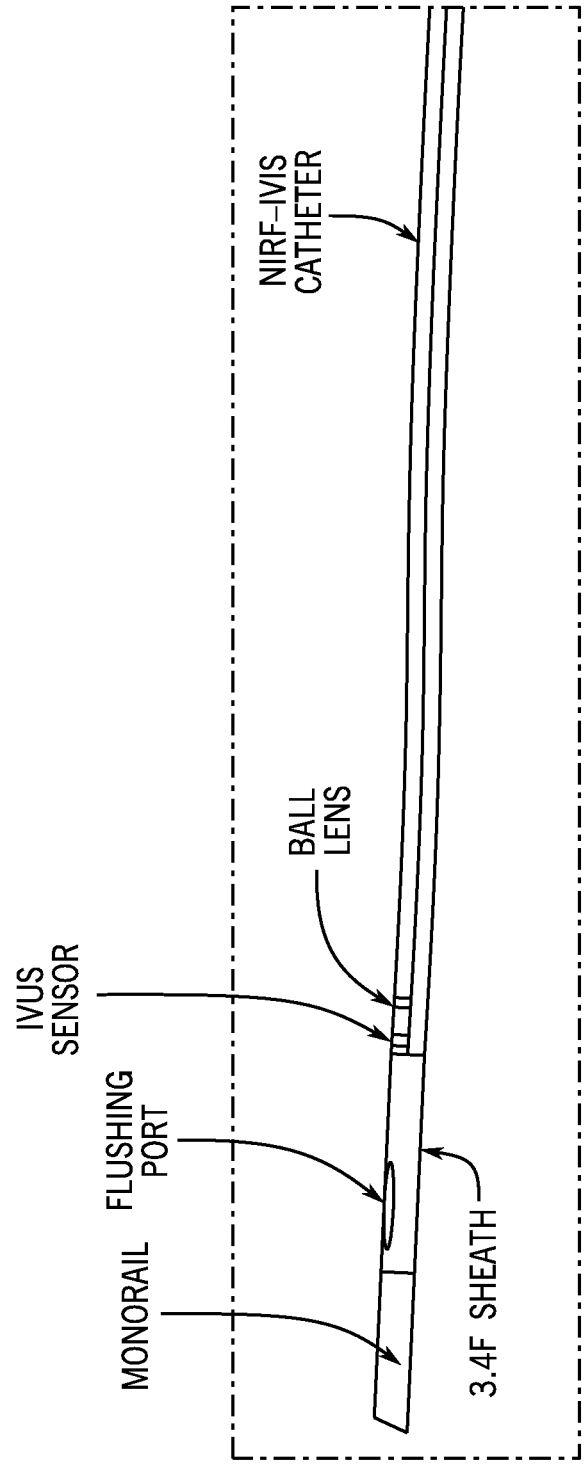

FIG. 6A illustrates a fully-assembled embodiment of the catheter of the invention, equipped with key structural features of the invention configured for clinical application, while FIG. 6B shows the embodiment of the catheter inserted in a 3.4 F catheter sheath.

Figures 7, 8:
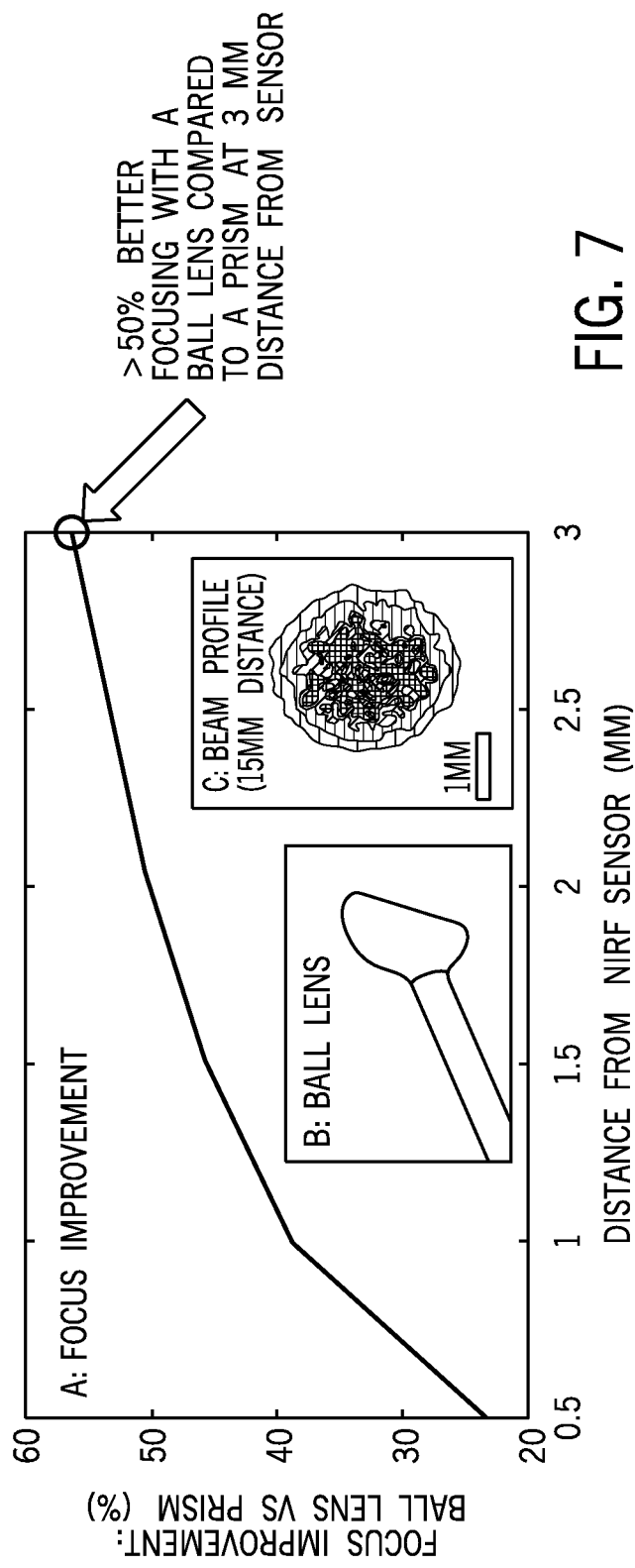
FIG. 7 contains plot A, illustrating the improvement of the quality of the focal spot of optical radiation as a function of distance from the sensor, outcoupled from the optical channel of the embodiment of the catheter during its operation, with that of related art that utilized an optical prismatic element. Inserts B and C illustrate, respectively, an optical fiber terminated with the lens structured according to an embodiment of the invention, and a cross-section profile of the optical beam at a distance of about 15 mm from the lens of the optical channel
FIG. 8 is a table summarizing structural and/or material and/or operational characteristics of a) hybrid imaging probe of related art (designated in the table as v.1.0 and containing an optical-signal-transmitting member and an electrical-signal transmitting member being parallel to one another and the optical prism, configured to couple light into and out-couple light from the optical-signal-transmitting member in parallel and next to the acoustic transducer, per FIG. 1C; tested in vivo); b) an embodiment of the probe according to the idea of the invention (denoted as v. 2.0, with a serial/sequential positioning of the optical transceiver, which includes a truncated lens element, and the acoustic transducer on the axis of the probe tested in vitro). Cross-sectional dimension of the the catheter sheath (outlining the body of the probe) does not exceed 1.2 mm and the body of the probe inside the sheath does not exceed 0.7 mm in cross-sectional dimension thereof; and c) a further reduced in dimensions embodiment of v. 2.0 (denoted in the table as v. 3.0).
Figure 16A:
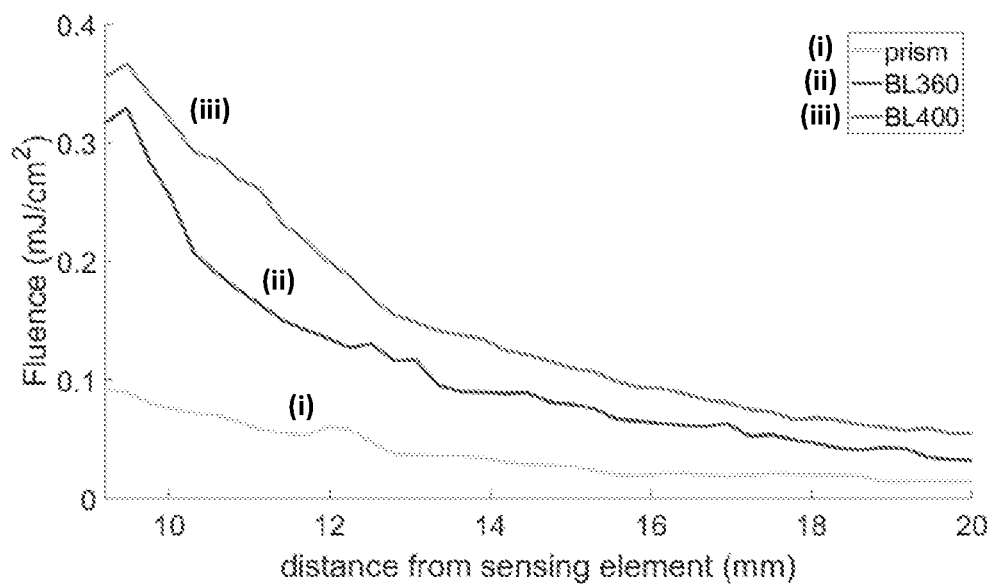
FIG. 16A contains plots presenting the comparison among the empirically acquired data representing optical fluence measured with a beam profiler as a function of distance from the sensing element. The outputs from the optical channel of the probe terminated with the 400 um diameter truncated ball lens (BL400) and the 360 um diameter truncated ball lens (BL360) demonstrate almost 4-fold and 3-fold, respectively, higher fluence as compared to an embodiment employing the optical prism at the end of the otherwise identical optical channel.
Figure 16B:
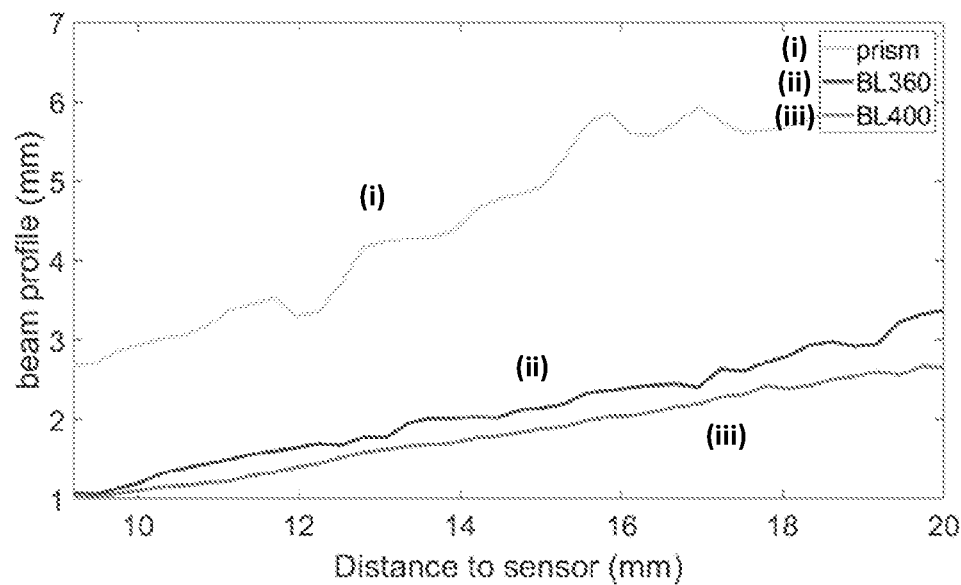
FIG. 16B: Beam profiles measured with a beam profiler as a function of distance from the sensors. The 400 um diameter truncated ball lens (BL400) and the 360 um diameter truncated ball lens (BL360) show smallest beam widths as compared to the prism-based embodiment of related art.

FIG. 7 is a plot A, illustrating the calculated improvement of the quality of the focal spot of optical radiation, outcoupled from the optical channel of the embodiment of the catheter during its operation, with that of related art that utilized an optical prismatic element. Ball lens 120 was assumed to have a 400 micron diameter (with an aperture of 250 micron by 250 micron), forming a beam of light with beam width of less than 1 mm at a distance of 10 mm from the ball lens (the ISO11146-defined level). (As an example, consider, for the purpose of simplicity—a ball lens that is intact and that has not been yet polished to form the facet 120A. The numerical aperture NA is a function of the ball lens diameter D, index of refraction n, and diameter d of a beam from the input source d: $NA=n*\sin(\theta)=1/(\sqrt{1+4(nD/(4d(n-1))^2}$. Accordingly, NA=0.1 for D=360 um, n=1.454, and d=50 um.) Further, FIGS. 16A, 16B provide empirical evidence that a) embodiments of the invention provide higher fluence of excitation light on the target as compared with prism-based embodiments of related art, thereby causing increase in the NIRF sensitivity of the measurement, and that b) embodiments of the invention form optical beams that are spatially-reduced as compared with the otherwise identical optical channels cooperated with an optical prism (as per related art).

A skilled artisan readily appreciates that the optical prism used in embodiments of related art lacks the ability to focus the beam of radiation, as a result of which the FWHM of the beam at the same 3 mm distance of the prism exceeds 1 mm in dimension. Accordingly, the embodiment of the invention demonstrates more than 50% improvement in optical quality of the corresponding spot at a distance of 3 mm from the lens, and >20% improvement in focusing at a distance of 0.5 mm from the fiber. Therefore, a truncated-ball-lens-based design of the optical transceiver enables higher fluence at the tissue target, thereby resulting in higher signal-to-noise ratio (SNR)—and, accordingly, the higher spatial resolution—as compared to the prism-based design of related art, due to better focusing of outcoupled optical beam.

In reference to the summary of catheter parameters of FIG. 8, the version 3.0 F of the hybrid NIRF/IVUS catheter was constructed with the use of a coaxial wire (200 V rating, outer diameter of 160 microns) as an electrically-conducting member configured for transmission of an electrical signal to which the ultrasound signal is transformed with the use of the acoustic transducer and for pulse-echo imaging. The IVUS transducer (for example, utilizing the PZT, pvdF, PMN-PT, PZN-PT) such as the transducer currently used for clinical IVUS imaging at the 40 MHz central frequency (or, in a related embodiment—the one operating at a central frequency of up to 100 MHz) as well as broadband sensor covering a range of frequencies from <10 MHz up to 60 MHz and even higher. The central frequency and the detection bandwidth, however, are not limited to this frequency range, but can also be at higher frequency level such as 60 MHz, 80 MHz, and/or 100 MHz or, alternatively, at a lower frequency level such as at 30 MHz, 20 MHz, and/or 10 MHz with detection bandwidth of >100%. (Here, the width BW of the detection band is conventionally numerically denoted in reference to the central frequency $f_{ctr}$ and at a level of −6 dB. In other words, the value of the difference between $f_{hi}=f_{ctr}+(f_{hi}*BW/2)$ and $f_{low}=f_{ctr}-(f_{ctr}*BW/2)$ in this case is greater than the value of $f_{ctr}$.) The ball lens (with a diameter of about 320 microns or about 360 microns in a related embodiment) was optically affixed to the MMF 160 (core diameter 50 microns; cladding diameter 125 microns; outer diameter 250 microns) while polished to form a substantially-planar surface 120A at an angle α of about 6 degrees, thereby enabling the appropriate redirection of light arriving at the lens 120 from the fiber 160 to maximize the spatial overlap between the acoustic and optical beams emanating from the probe towards the surrounding medium (see FIG. 5A).

It is understood that the polishing angle α may be changed and customized to fit the size of a catheter in a particular implementation (as well as the geometry of the used sensors, the size of the target vessel, etc) in related embodiments, and that a SMF or a double-clad fiber/DCF can be used instead of the MMF. The heat-shrinking tube was used to construct the fluid (preferably—gas)-filled chamber 152. (In one embodiment, the chamber 152 was filled with air to maintain a refractive index of 1 such that the optical properties of the light beam transmitted between the optical member 160 and the target vessel—and, in particular, the focusing parameters of the lens 120—remained constant when operating the embodiment of the catheter in liquid environment.) The Asahi torque coil 154 (with the outer diameter of 0.55 mm, the inner diameter of 0.45 mm) was used. Ferrule/housing 210 for the optical/acoustic sensors was customized and made from stainless steel with two openings in the side wall of the ferrule, spatially corresponding to the locations of the sensors along the axis of the probe. Polyurethane adhesive was used as sealant in one implementation of the catheter. (In a related embodiment, the substantially-planar surface 120A of the lens 120 can be coated with high-reflectance coating for the polished truncated ball lens to be employed in liquid/water: here, such optical transceiver can be positioned immediately next to and sequentially with the acoustic transducer on the axis of the probe, in the same liquid medium with refractive index exceeding 1, in which case the separate fluid-filled chamber containing the optical transceiver is not required.)

Peripheral Sub-Systems

Figure 11:
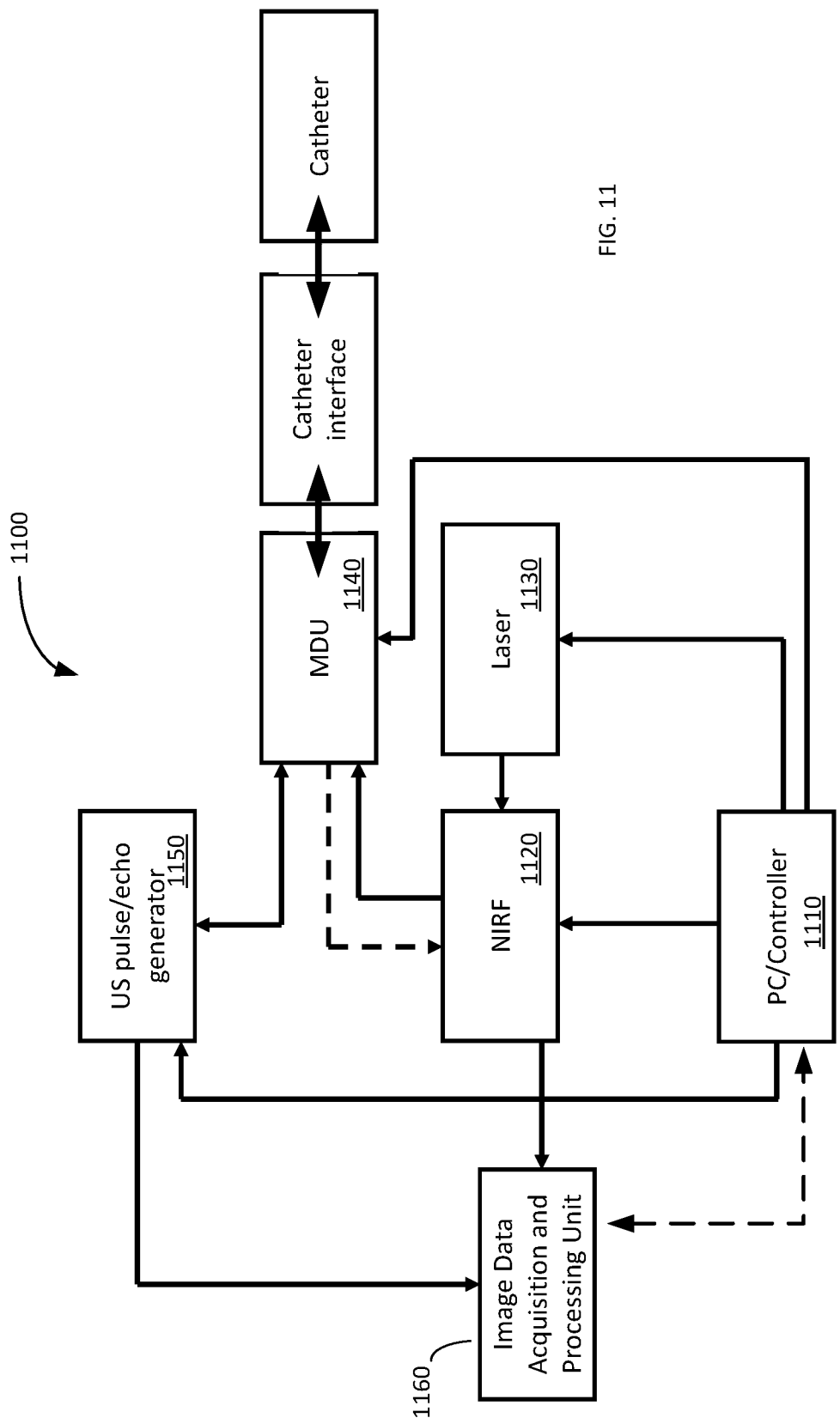
FIG. 11 presents a simplified schematic of the peripheral portion(s) of an embodiment of the imaging system.

FIG. 11 is a simplified schematic of an embodiment 1100 of the imaging system of the invention detailing some of the sub-systems and/or components of the system used, in operation, for collection and processing empirical data and for forming informative output(s) at least some of which are visually-perceivable by the user of the system. (As a skilled artisan will readily understand, the schematic of FIG. 11 should be appreciated in light of and in conjunction with the above-presented description of tangible component(s) of embodiment(s) of the probe.)

As shown, the operation of the embodiment 1100 of the imaging system is governed with the programmable processor 1110 (such governing may be effectuated with the use of an appropriately-configured computer-program product, encoded in a non-transitory tangible computer-readable storage medium and containing program code(s) for carrying out the steps of operation of the imaging system; not shown). The programmable processor 1110 is operably cooperated to electronically communicate and exchange data with at least the NIRF sub-system 1120, the source of laser radiation 1130, the motor-drive unit (MDU) sub-system 1140, with the acoustic (ultrasound) pulse/echo generator 1150, and with the electronic circuitry 1160, configured to acquire various data from the component and sub-systems of the system 1100 and to process these data to generate a user report and/or other tangible information-containing output (such as, for example, a visually-perceivable image). The embodiment of the catheter is operably connected to the MDU 1140 with a catheter interface which includes a fiber-optic connector and an RF connector.

Figure 12:
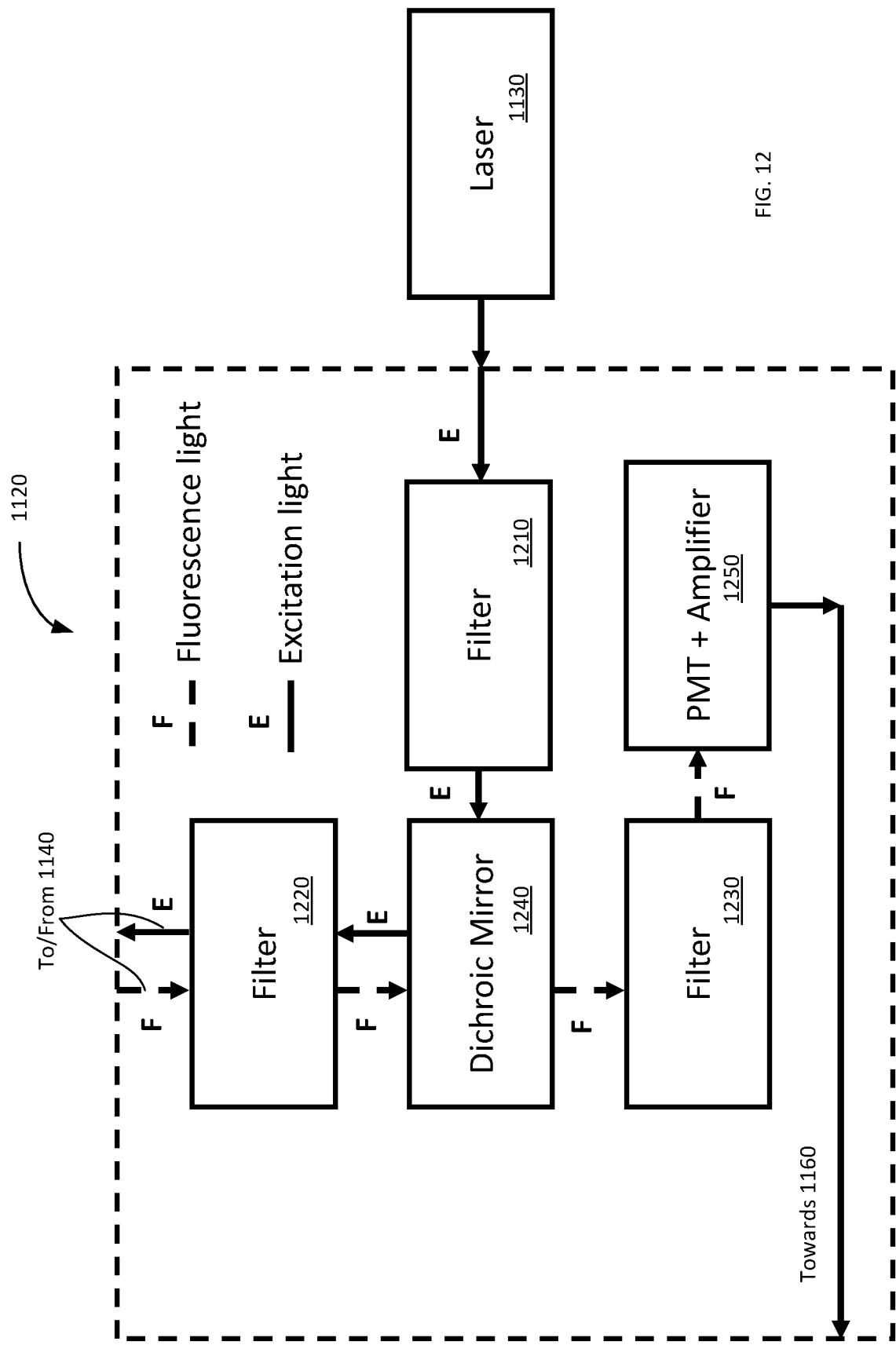
FIG. 12 is a schematic of an embodiment of the NIRF sub-system of the invention.

Schematic of the NIRF sub-system 1120, configured to transform and/or process excitation light (E, e.g. narrow-band, or monochromatic, or light of a specific optical bandwidth) received from the source of light 1130 (shown as a laser source, but optionally a photodiode or an LED) and fluorescence (F) acquired from the MDU sub-system 1140, is illustrated in FIG. 12. The sub-system 1120 includes optical filters 1210, 1220, 1230 (configured to transmit light within pre-determined portion(s) of the optical spectrum; a dichroic optical reflector 1240; and an optical detection device 1250 (shown in this example as a combination of a photomultiplier tube with an appropriate amplifier), configured to detect photons from fluorescence emission, amplify the corresponding fluorescence signal, and convert the fluorescence signal to an electric signal that is further acquired by the DAQ 1310. In a related embodiment, the dichroic filter configured to separate the excitation light from the fluorescent optical signal can also be realized with an optical circulator (in a three-port implementation), whereby the excitation light is directed to/at a first port, the second port is associated with both the excitation light and the fluorescent light, and the third port is operably associated with fluorescent light.

Figure 13:
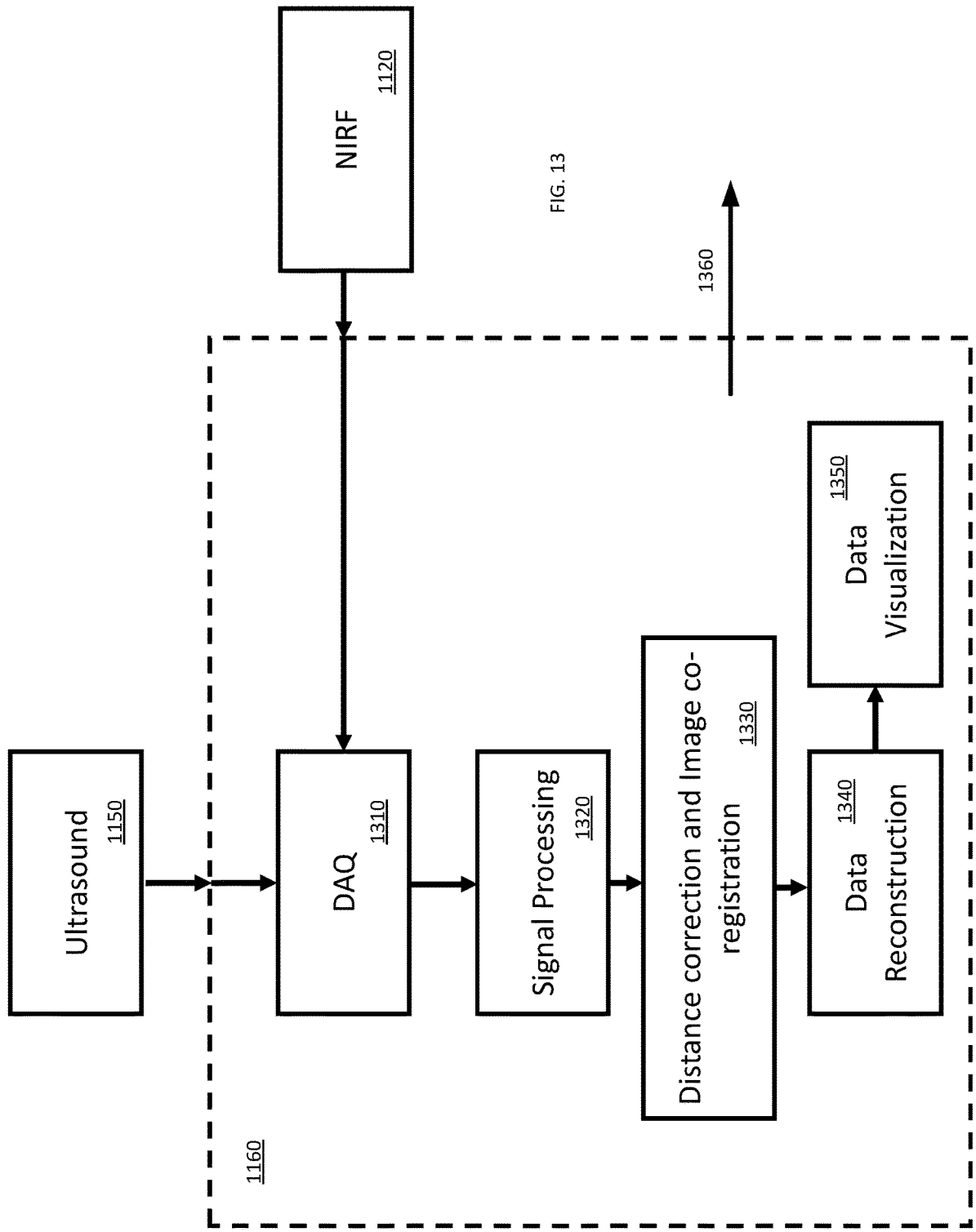
FIG. 13 is a schematic of an embodiment of the image-data acquisition and data processing sub-system of the invention.

FIG. 13 presents an embodiment of the image data acquisition and processing sub-system containing electronic circuitry 1160 that includes electronics configured to carry out at least data-acquisition 1310, signal-processing 1320, distance correction and image-co-registration 1330, data-reconstruction 1340, and/or data visualization 1350. Specifically, the circuitry 1160 acquired a fluorescence signal (NIRF) and an ultrasound signal (IVUS) for later processing. The device for data visualization 1350 may be represented by a monitor or display, for example, configured to form (for example, on a screen of a monitor or display) a visually-perceivable image representing chosen information (whether an ultrasound or fluorescent image of the target or an image depicting some intermediate step of the imaging procedure or an image representing the desired comparison between identified empirically-acquired data sub-sets).

Figure 14:
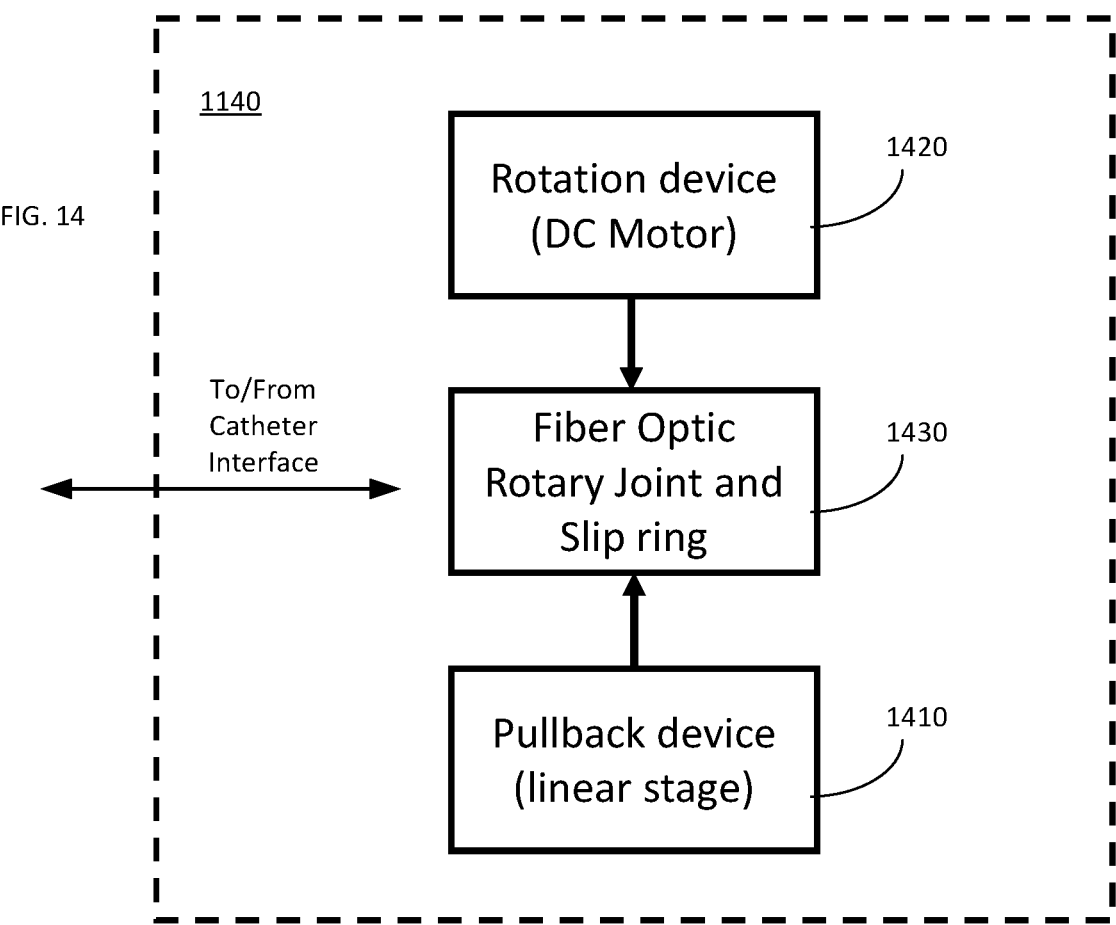
FIG. 14 illustrates a motor-drive (electro-mechanical) device providing an operational interface between the peripheral sub-systems of the imaging system of the invention and an embodiment of probe with which the system is equipped.

The motor-drive unit 1140, an embodiment of which is schematically shown in FIG. 14. Components of the unit 1140 include a pull-back device 1410 (structured around a liner repositioning stage), a DC motor 1420, and a judiciously designed combination of a fiber-optic rotary joint (FORJ) and a slip-ring 1430, to enable the acquisition of 3D image data from the catheter interface. (Detailed examples of types and constructions of optical rotary joints and slip-rings can be found in related art literature.)

Figure 15:
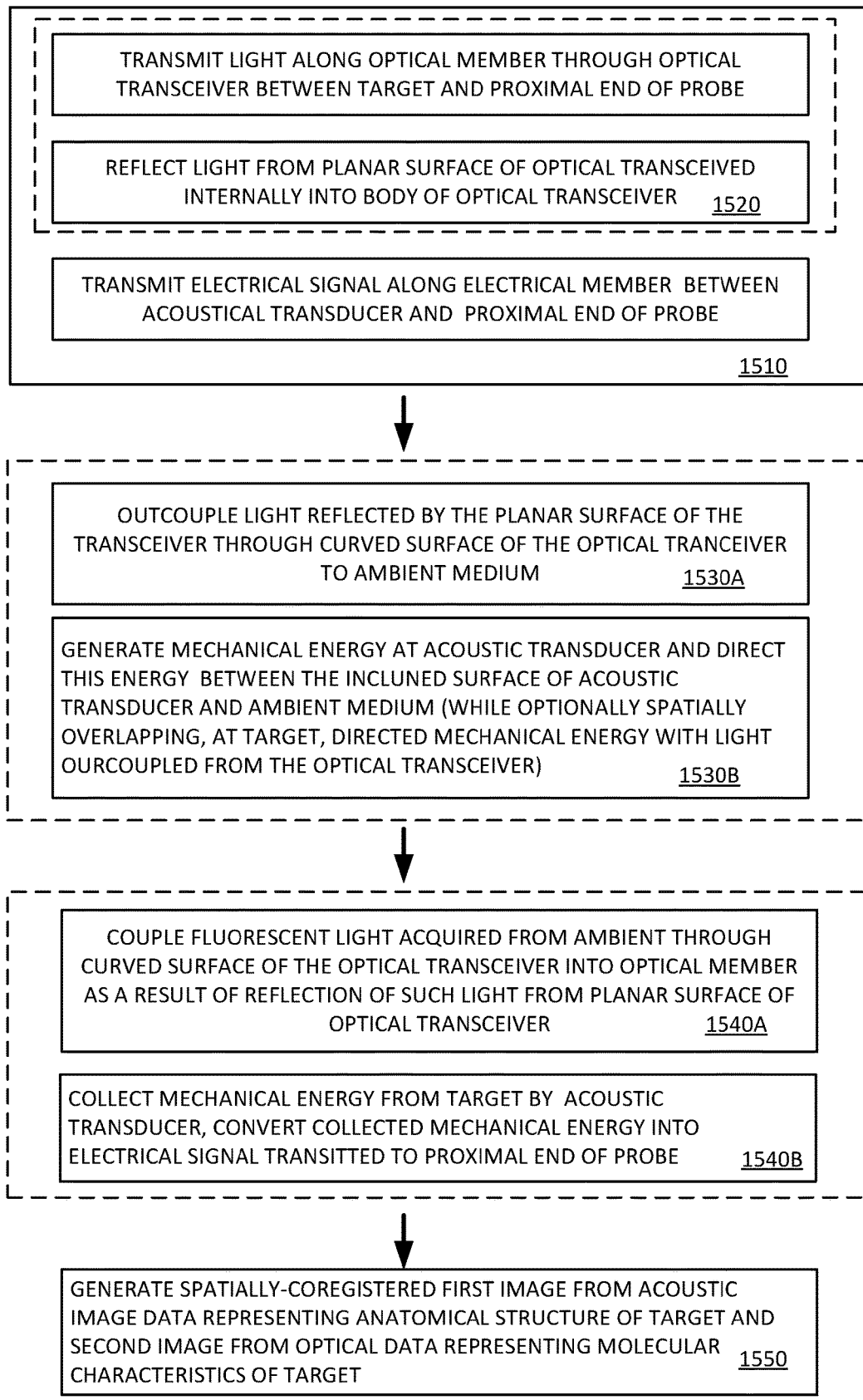
FIG. 15 is a flow-chart illustrating selected steps of the method for operation of an embodiment of the invention.

It is appreciated, therefore, that with the use of the embodiment of the NIRF/IVUS probe of the invention cooperated with the above-discussed peripheral sub-systems, an imaging system of the invention is configured to acquire (spatially co-registered) optical and ultrasound images of a bodily vessel through which the probe may be repositioned as a results of the pull-back procedure, for example. An example of a method for operating an embodiment of the imaging probe (such as the probe 300 of FIG. 3) of the invention is schematically illustrated with a flow chart of FIG. 15. Here, the probe is operated by, 1510, transmitting light inside an optical member that extends along the axis inside the sheath of the probe between and connects the proximal end of the probe and an optical transceiver and transmitting an electrical signal via an electrically-conducting member extending inside the sheath parallel to the optical member and connecting the proximal end of the probe and an acoustic transducer. The acoustic transducer and the optical transceiver are disposed in sequence with one another along the axis of the probe. Light transmitted along the optical member is reflected, at 1520, from a substantially-planar surface of the optical transceiver (which surface is inclined with respect to an optical axis of the optical member) internally into a body of the optical transceiver. (Light transmitted along the optical member includes light at the excitation wavelength (delivered from the laser source through the optical member and the optical transceiver to the target vessel outside the probe and/or the fluorescent light, generated at the target vessel as a result of the vessel's being irradiated with the light at the excitation wavelength.) The method may additionally include the steps of at least one of: a) outcoupling light, reflected internally into the body of the optical transceiver by the substantially-planar surface of the optical transceiver, through a spatially-curved surface of the optical transceiver into an ambient medium surrounding the optical transceiver to form a first beam of excitation light, (at 1530A) and b) generating an acoustic beam at the ultrasound transducer inclined with respect to the axis of the probe (at 1530B). Both of the optical and acoustic beams, emanated from the distal portion of the probe into the surrounding medium at these steps, are directed such as to define an area or volume of space where these two beams overlap with one another.

After the probe is oriented such that this area or volume of space (where the optical excitation beam and the acoustic excitation beam overlap) is positioned at the location of the target of interest (a bodily vessel, for example), and in response to being irradiated with excitation light and/or the acoustic beam, the target vessel generates, respectively, fluorescence representing molecular structure of the target and ultrasound signal representing the anatomical structure of the target. At this time, step 1540A occurs, with coupling of fluorescent light (collected by the optical transceiver through the spatially-curved surface of the optical transceiver from the ambient medium and reflected internally into the body of the optical transceiver by the substantially-planar surface) into the optical member to form a fluorescence signal delivered to the proximal end of the probe and further to the peripheral sub-systems of the imaging system of the invention. At either substantially the same time or at a different time, an acoustic signal generated by the target is collected at the ultrasound transducer and transformed to the electrical signal to be passed along the electrical member towards the peripheral sub-systems of the imaging system, as step 1540B. At step 1550, spatially co-registered fluorescent-signal-based and acoustic-signal-based images of the target are being formed with the use of the programmable processor and the display (not shown) of the imaging system. After further post-processing of signals, a distance correction algorithm may be applied in order to generate quantitative NIRF images displaying molecular concentrations of the imaged fluorophore/fluorescence emitting target co-registered on the anatomical IVUS image in a blended NIRF-IVUS image. Distance correction is performed, for example, by calculating the concentration of the imaged fluorescence target based on a model of light absorption and scattering with known distances from IVUS images.

To this end, FIGS. 9, 10A, 10B, 10C illustrate the empirical results obtained with an embodiment of the invention. FIG. 9 depicts an optical signal (spot of light 910) acquired during the in vitro pull-back of an embodiment 920 of the catheter of the invention in a rabbit aorta. FIG. 10A shows a 3.4 F embodiment 1012 of the catheter of the invention a resected aorta vessel. Capillary tube 1020 with AF750 dye is positioned next to the catheter 910 in the vessel to enable contrast of the NIRF image. FIG. 10B presents an overlap of the NIRF image (optical signal 1024) and the IVUS image (gray portion of the image) showing the aorta and the capillary tube in both images. FIG. 10C: a depth-profilometric (spatially unwrapped pull-back) IVUS image of FIG. 10B of the aorta vessel.

In accordance with examples of embodiments, an imaging probe, an imaging system containing such probe, and a method for operating such imaging system and/or imaging probe are provided. An embodiment of the imaging system, for example, is configured to generate spatially-co-registered first and second images (the first image representing an anatomical structure of a target, the second image representing a molecular structure of the target) and includes an imaging catheter having an axis, proximal and distal ends, and optically-transparent member and an electrically-conducting member; a motor-drive sub-system, including an optical rotary joint and a slip-ring, such that the motor-drive sub-system is operably attached to the proximal end; a source of excitation light optically-connected with the optically-transparent member through the optical rotary joint; and an ultrasound pulse generator electrically-connected with the electrically-conducting member through the slip-ring. The optically-transparent member extends from the proximal end to the distal end of the probe in parallel to the axis and is attached to an optical lens (a body of which is contained between a spatially-curved surface and a substantially-planar surface, the optical lens being affixed to the optically-transparent member at the spatially-curved surface such that the substantially-planar surface is inclined with respect to an axis of the optically-transparent member). The electrically-conducting member also extends from the proximal end to the distal end of the probe in parallel to the optically-transparent member and is terminated with an acoustic transducer. The acoustic transducer and the optical transceiver are disposed sequentially on the axis of the catheter. In one case, there is a housing element at least partially-enclosing the optically-transparent member, the optical transceiver, the electrically-conducting member, and the acoustic transducer. The housing element is dimensioned to not exceed 1.2 mm in diameter. Substantially in any implementation of the imaging system of the invention, the system may additionally include a programmable computer processor and tangible, non-transitory storage medium containing program code thereon which, when downloaded onto the programmable processor, causes the programmable processor to effectuate at least one of the following processes: (a) to operate, in time-coordinated fashion, the source of excitation light and the ultrasound pulse generator to deliver the excitation light and electrical pulses to the optical lens and the acoustic transducer, respectively; (b) to change a position of the catheter with respect to a chosen target while, at the same time, collecting a return electrical signal and a return optical signal respectively representing an acoustic wave generated at the target and a fluorescent light generated at the target; and (c) to form spatially co-registered first and second images based on return electrical signal data and return optical signal data. Notably, the catheter of the imaging system is devoid of (that is, does not contain) an optical prism.

While specific values chosen for these embodiments are recited, it is to be understood that, within the scope of the invention, the values of all of parameters may vary over wide ranges to suit different applications.

Embodiments of the imaging system of the invention and their operations have been described as including a processor controlled by instructions stored in a memory. The memory may be random access memory (RAM), read-only memory (ROM), flash memory or any other memory, or combination thereof, suitable for storing control software or other instructions and data. Some of the functions performed by the imaging system of the invention have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components. The scope of the invention includes an article of manufacture that contains a microprocessor, and a computer-readable medium (containing therein computer-readable program code for operating an imaging system equipped with a source of light, an electrical pulse generator, and an imaging probe that comprises and optical transceiver and an acoustic transducer disposed next to one another on an axis of the imaging probe). Here, the optical transceiver includes a substantially-planar surface that is inclined at a first angle with respect to the axis and the acoustic transducer includes a transducer surface that is inclined at a second angle with respect to the axis. The computer-readable program code contains a first series of computer-readable program steps to effect the steps of (a) generating excitation light at the source of light and electrical pulses at the electrical pulse generator in a time-coordinated fashion; and (b) forming first and second visually-perceivable representations of a target that has been (i) irradiated with excitation light delivered to the target upon reflection of the excitation light from the substantially-planar surface, and (ii) insonated with an acoustic beam delivered from the acoustic transducer. Here, the first visually-perceivable representation is formed in light having a wavelength that is longer than a wavelength of the excitation light, and the first and second visually-perceivable representations are spatially-co-registered as a result of said first and second angles being non-zero angles. In such article of manufacture, the computer-readable program code may optionally contain a second series of computer-readable program steps to effect repositioning a distal end of said imaging probe with respect to the target while rotating said distal end about the axis at an angle of up to 360 degrees.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. When used in reference to a numerical value, represent a range of plus or minus 20% with respect to the specified value, more preferably plus or minus 10%, even more preferably plus or minus 5%, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In some specific cases, which are within the scope of the invention, the terms "approximately" and "about", when used in reference to a numerical value, represent a range of plus or minus 20% with respect to the specified value, more preferably plus or minus 10%, even more preferably plus or minus 5%, most preferably plus or minus 2% with respect to the specified value.

While the invention is described through the above-described exemplary embodiments, it will be understood by those of ordinary skill in the art that modifications to, and variations of, the illustrated embodiments may be made without departing from the inventive concepts disclosed herein. For example, although some aspects of the method of the invention have been described with reference to a flowchart, those skilled in the art should readily appreciate that functions, operations, decisions, etc. of all or a portion of each block, or a combination of blocks, of the flowchart may be combined, separated into separate operations or performed in other orders. Moreover, while the embodiments are described in connection with various illustrative data structures, one skilled in the art will recognize that the system may be embodied using a variety of data structures. Furthermore, disclosed aspects, or portions of these aspects, may be combined in ways not listed above. Accordingly, the invention should not be viewed as being limited to the disclosed embodiment(s).

The invention claimed is:

1. A method for operating an imaging probe having an axis and an outer sheath, the method comprising:
   transmitting excitation light inside an optical member that extends along the axis inside the outer sheath between and connects a proximal end of the probe and an optical transceiver, which is directly affixed to a distal end of the optical member and secured in a fluidly sealed chamber that is filled with a fluid and that separates the optical transceiver from a liquid-filled lumen of the outer sheath, to deliver the excitation light from the optical member outside of the outer sheath through a first optical aperture defined by said chamber in the outer sheath in absence of a reflection off of a surface of an optical prism, and
   transmitting an electrical signal via an electrically-conducting member extending inside the sheath parallel to the optical member and connecting the proximal end of the probe and an acoustic transducer to generate a beam of acoustic energy at the acoustic transducer and to deliver said beam of acoustic energy from the acoustic transducer outside of the outer sheath through a second aperture defined by said chamber in the outer sheath,
   wherein the first optical aperture and the second aperture are spatially coordinated with the optical transceiver and the acoustic transducer, respectively,
   wherein the acoustic transducer is disposed sequentially with and at a distance from the optical transceiver along the axis, a wall of the fluidly sealed chamber separating the acoustic transducer and the optical transceiver.

2. The method according to claim 1, comprising:
   reflecting said excitation light from a substantially-planar surface of the optical transceiver, which is inclined with respect to an optical axis of the optical member, internally into a body of the optical transceiver and through said fluid inside the fluidly sealed chamber.

3. The method according to claim 1, further comprising at least one of the following:
   outcoupling said excitation light, delivered into a body of the optical transceiver in absence of the reflection off of the surface of the optical prism through said fluid inside the fluidly sealed chamber into an ambient medium surrounding the optical transceiver to form a first beam of excitation light; and
   coupling a first radiation, generated by the ambient medium as a result of absorption of the excitation light at the ambient medium, through the fluid and a spatially-curved surface of the optical transceiver into the optical member in absence of interaction of said first radiation with the surface of the optical prism to form a fluorescence signal delivered to the proximal end.

4. The method according to claim 1, wherein said transmitting excitation light includes transmitting the excitation light through the optical transceiver that is directly attached to the distal end of the optical member at a spatially-curved surface of the optical transceiver.

5. The method according to claim 1, wherein said transmitting excitation light inside the fluidly sealed chamber includes transmitting the excitation light through gas.

6. The method according to claim 1, wherein each of said transmitting the excitation light inside the optical member and said transmitting the electrical signal via the electrically-conducting member includes transmitting energy inside a coil disposed inside the outer sheath that has having a diameter smaller than 1.2 millimeters.

7. The method according to claim 1, wherein each of said transmitting the excitation light inside the optical member and said transmitting the electrical signal via the electrically-conducting member includes transmitting energy inside a coil disposed inside the outer sheath that has a diameter smaller than 0.7 millimeters.

8. The method according to claim 1, further comprising:
with the use of optoelectronic circuitry operably cooperated with the proximal end of the probe,
   a) receiving a return electrical signal acquired with the acoustic transceiver from a first location outside of the sheath to form a first image representing an anatomical structure at the first location; and
   b) receiving a return optical signal acquired in transmission through the fluid and the optical transceiver from a second location outside of the sheath to form a second image of a molecular structure characterizing said second location, wherein the return optical signal contains fluorescence generated at the target in response to the target being irradiated with the excitation light delivered from a proximal end of the optical member and reflected by the substantially-planar reflector internally into a body of the optical transceiver.

9. The method according to claim 1, further comprising generating mechanical energy and directing said mechanical energy between a surface of the acoustic transducer, that is inclined with respect to the axis, and a target.

10. The method according to claim 9, wherein at least one of the following conditions is satisfied:
   a) wherein the mechanical energy includes a first acoustic beam generated by the acoustic transducer; and comprising;
      spatially overlapping a first beam of the excitation light, outcoupled through the sheath from the optical transceiver upon reflecting said light from a substantially-planar surface of the optical transceiver and transmitting said light through a spatially-curved surface of the optical transceiver, with said first acoustic beam delivered through the sheath, to define an area both irradiated with the first excitation beam and insonated with the first acoustic beam; and
   b) wherein the mechanical energy includes a second acoustic beam formed at the target in response to the target being insonated with the first acoustic beam.

11. The method according to claim 10, comprising;
positioning said area at the target to cause the target to produce a fluorescent light and an acoustic energy; and
collecting said fluorescent light by the optical member upon reflecting said fluorescent light by the substantially-planar surface while transforming said acoustic energy to a return electrical signal to co-register the fluorescent light and the return electrical signal by electronic circuitry operably connected to the probe at the proximal end.

12. The method according to claim 10, wherein said spatially-overlapping includes spatially-overlapping said first beam of said excitation light and said first acoustic beam at a location on a plane containing the axis of the probe.

13. A method for operating an imaging probe having an axis and an outer sheath, the method comprising:
transmitting excitation light inside an optical member that extends along the axis inside the outer sheath between and connects a proximal end of the probe and an optical transceiver, which is directly affixed to a distal end of the optical member and secured in a fluidly sealed chamber that is filled with a fluid and that separates the optical transceiver from a liquid-filled lumen of the outer sheath, to deliver the excitation light from the optical member outside of the outer sheath through a first optical aperture defined by said chamber in the outer sheath in absence of a reflection off of a surface of an optical prism,
transmitting an electrical signal via an electrically-conducting member extending inside the sheath parallel to the optical member and connecting the proximal end of the probe and an acoustic transducer to generate a beam of acoustic energy at the acoustic transducer and to deliver said beam of acoustic energy from the acoustic transducer outside of the outer sheath through a second aperture defined by said chamber in the outer sheath,
wherein the first optical aperture and the second aperture are spatially coordinated with the optical transceiver and the acoustic transducer, respectively,
wherein the acoustic transducer is disposed sequentially with and at a distance from the optical transceiver along the axis, a wall of the fluidly sealed chamber separating the acoustic transducer and the optical transceiver, and
wherein the optical member is configured to transmit said excitation light in a core of the optical member, and further comprising transmitting a return light through a cladding of the optical member, said return light emitted at a location outside of the sheath in response to absorption of said excitation light at the location.

14. An imaging probe configured to generate spatially-co-registered first and second images, the first image representing an anatomical structure of a target, the second image representing a molecular structure of the target, the imaging system comprising:
an imaging catheter having an axis and proximal and distal ends and including,
   i) an optically-transparent member extending from the proximal end to the distal end of the imaging catheter in parallel to the axis;
   ii) an optical lens having a body contained between a spatially-curved surface and a substantially-planar surface, the optical lens being directly affixed to the optically-transparent member at the spatially-curved surface such that the substantially-planar surface is inclined with respect to an axis of the optically-transparent member; and
   iii) an electrically-conducting member that extends from the proximal end to the distal end of the imaging catheter in parallel to the optically-transparent member and that is terminated with an acoustic transducer,
   wherein a portion of the optical member and the optical lens are disposed inside a fluidly-sealed chamber containing a fluid and separating the optical lens from a liquid-filled lumen of the imaging catheter,
   wherein the acoustic transducer and the optically-transparent member are disposed sequentially on the axis of the catheter inside a coil, wherein said imaging catheter contains a first optical aperture and a second aperture defined in a wall thereof, the first and second apertures separated from one another along a length of the imaging catheter, wherein the first optical aperture is spatially coordinated with the optical lens and said fluidly-sealed chamber to have optical energy exchanged between said optical lens and outside of the imaging aperture be transmitted through said first optical aperture, wherein the second aperture is spatially coordinated with the acoustic transducer to have acoustic energy exchanged between the acoustic transducer and the outside of the imaging catheter be transmitted through said second aperture;

a motor-drive sub-system, including an optical rotary joint and a slip-ring, the motor-drive sub-system operably attached to the proximal end; and a source of excitation light optically-connected with the optically-transparent member through the optical rotary joint, and an ultrasound pulse generator and echo detector electrically-connected with the electrically-conducting member through the slip-ring.

15. The imaging probe according to claim 14, further comprising a housing element at least partially-enclosing said optically-transparent member, said optical transceiver, said electrically-conducting member, said coil, and said acoustic transducer, said housing element dimensioned to not exceed 1.2 mm in diameter.

16. The imaging probe according to claim 14, further comprising a programmable computer processor and tangible, non-transitory storage medium containing program code thereon which, when downloaded onto the programmable processor, causes the programmable processor to effectuate at least one of the following processes:

(i) to operate, in time-coordinated fashion, the source of excitation light and the ultrasound pulse generator to deliver the excitation light and electrical pulses to the optical lens and the acoustic transducer, respectively;

(ii) to change a position of the catheter with respect to a chosen target while, at the same time, collecting a return electrical signal and a return optical signal respectively representing an acoustic wave generated at the target and a fluorescent light that has been generated at the target and collected through the fluid and the optical member; and (iii) to form spatially co-registered first and second images based on return electrical signal data and return optical signal data;

(iv) to perform distance correction of the return optical signal data based on detected return electrical signal data to generate quantified near-infrared fluorescence (NIRF) molecular images.

17. The imaging probe according to claim 14, wherein the catheter is devoid of an optical prism.

* * * * *